United States Patent
Rastegar et al.

(10) Patent No.: US 9,913,758 B2
(45) Date of Patent: Mar. 13, 2018

(54) SHAPE AND PRESSURE ADJUSTABLE DRESSING

(75) Inventors: Jahangir S. Rastegar, Stony Brook, NY (US); Thomas Spinelli, Northport, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 918 days.

(21) Appl. No.: 13/607,690

(22) Filed: Sep. 8, 2012

(65) Prior Publication Data

US 2013/0237895 A1  Sep. 12, 2013

Related U.S. Application Data

(63) Continuation-in-part of application No. 13/459,246, filed on Apr. 29, 2012, now abandoned, which is a continuation-in-part of application No. 13/230,797, filed on Sep. 12, 2011, now Pat. No. 9,615,975, which is a continuation-in-part of application No. 13/046,767, filed on Mar. 13, 2011, now Pat. No. 8,604,266, which is a continuation-in-part of application No. 12/983,314, filed on Jan. 2, 2011, now Pat. No. 8,637,726.

(51) Int. Cl.
| | | |
|---|---|---|
| *A61F 13/02* | (2006.01) | |
| *A61F 13/00* | (2006.01) | |
| *A61B 17/08* | (2006.01) | |
| *A61B 17/00* | (2006.01) | |

(52) U.S. Cl.
CPC ........ *A61F 13/02* (2013.01); *A61F 13/00021* (2013.01); *A61F 13/00038* (2013.01); *A61F 13/023* (2013.01); *A61B 17/083* (2013.01); *A61B 17/085* (2013.01); *A61B 2017/00867* (2013.01); *A61F 2013/0028* (2013.01)

(58) Field of Classification Search
CPC .................. A61F 13/02; A61F 13/025; A61F 2013/00119; A61F 2013/00165; A61F 2013/00238; A61F 2013/0028; A61B 17/085; A61B 17/08; A61B 17/10; A61B 17/83; A61B 2017/00884; A61B 2017/086
USPC .................. 602/41–44, 52, 54, 58; 606/213, 606/215–216
See application file for complete search history.

(56) References Cited

U.S. PATENT DOCUMENTS

| | | |
|---|---|---|
| 4,706,661 A | 11/1987 | Barrett |
| 4,865,026 A * | 9/1989 | Barrett .......................... 606/214 |
| 7,834,232 B2 | 11/2010 | Rastegar et al. |
| | (Continued) | |

FOREIGN PATENT DOCUMENTS

FR  1428500 A  *  1/1966

OTHER PUBLICATIONS

FR1428500 Machine Translation.*
(Continued)

*Primary Examiner* — Kari Rodriquez

(57) ABSTRACT

A method of closing a wound with a dressing. The method including: restraining at least a portion of the dressing corresponding to the wound into a first shape; adhering first and second portions of the dressing across the wound; removing the restraint from the dressing while the first and second portions are adhered to the skin by removing a member from the dressing to allow at least the portion to move towards a second shape and apply a force tending to close the wound.

7 Claims, 41 Drawing Sheets

(56) References Cited

U.S. PATENT DOCUMENTS

| | | |
|---|---|---|
| 2008/0146982 A1 | 6/2008 | Rastegar et al. |
| 2008/0167593 A1 | 7/2008 | Fleischmann |
| 2008/0306456 A1 | 12/2008 | Riesinger |
| 2010/0318052 A1 | 12/2010 | Ha et al. |
| 2011/0036306 A1* | 2/2011 | Chao ............................. 119/850 |
| 2013/0282049 A1* | 10/2013 | Peterson et al. ......... 606/204.45 |

OTHER PUBLICATIONS

International Search Report dated Dec. 4, 2012 received in corresponding International Application No. PCT/GB2012/052256.
International Search Report dated Dec. 4, 2012 received in corresponding International Application No. PCT/GB2012/052258.

* cited by examiner

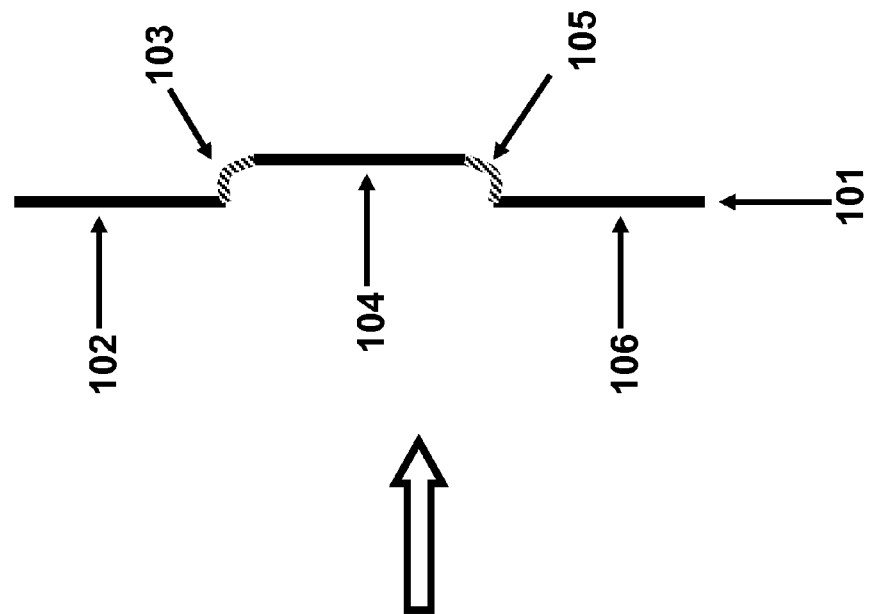
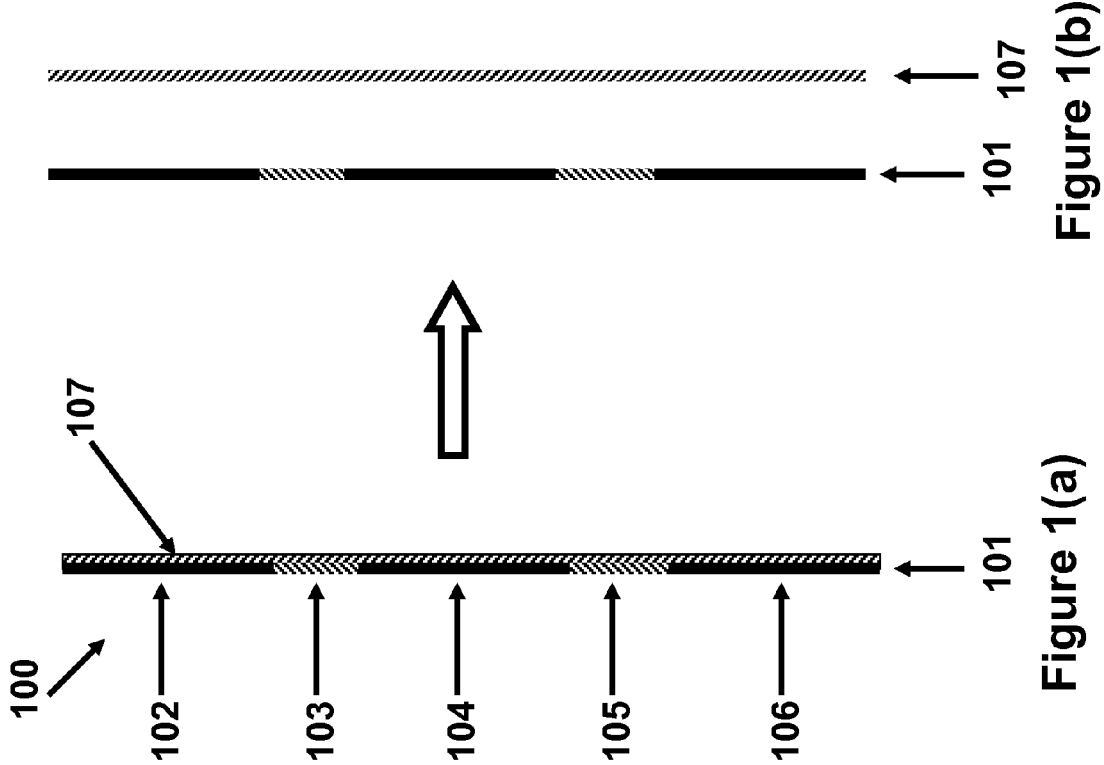

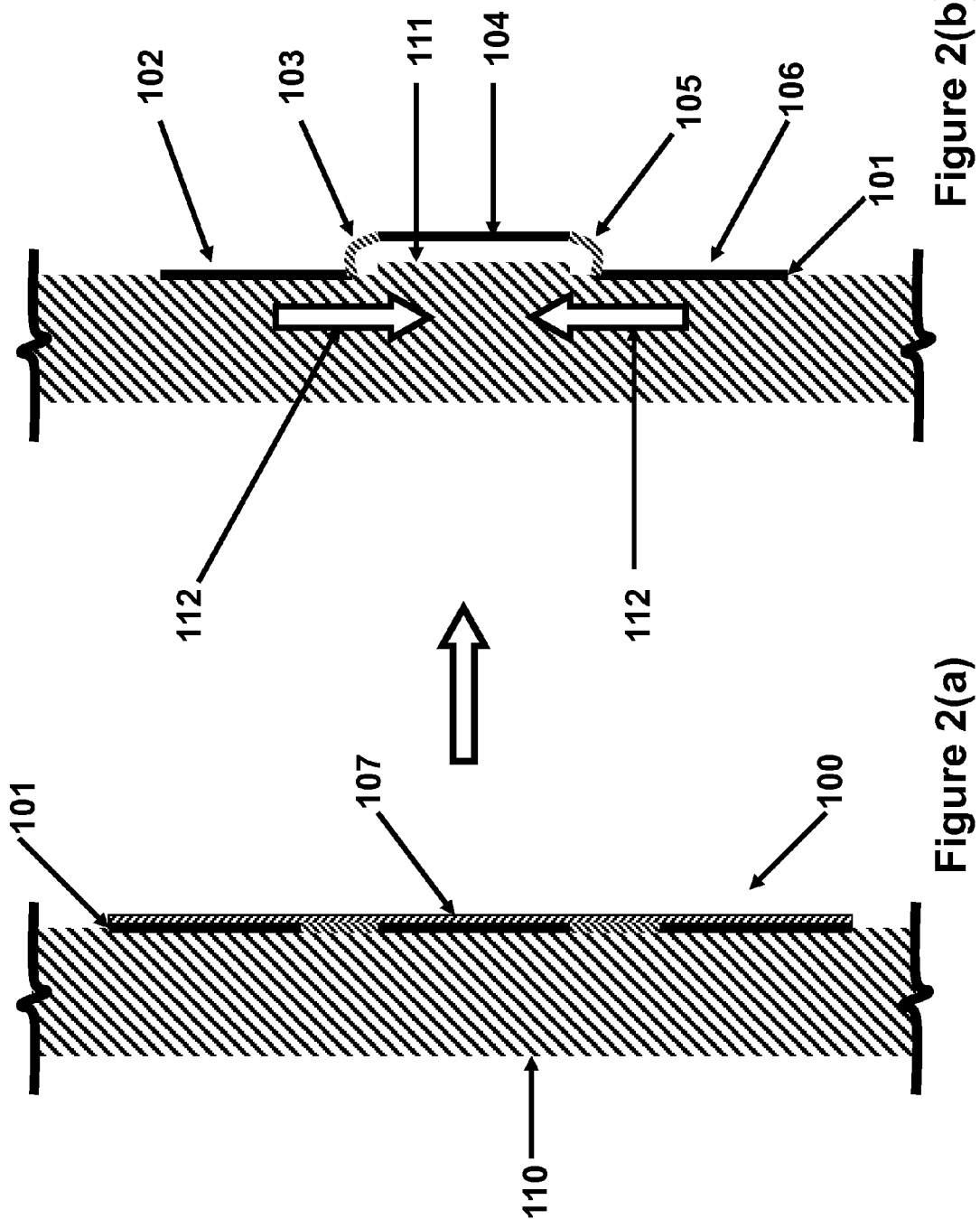

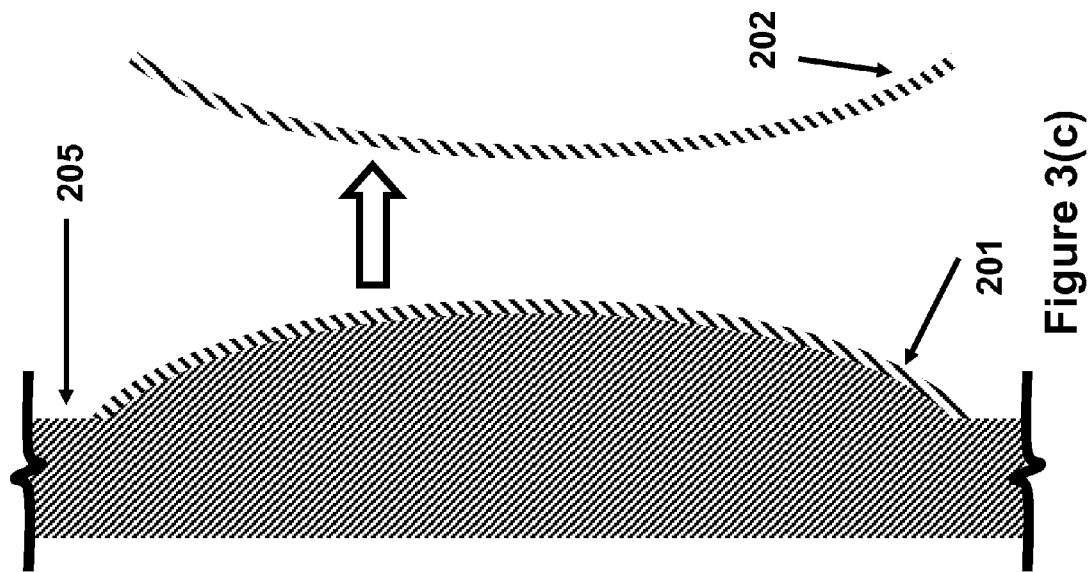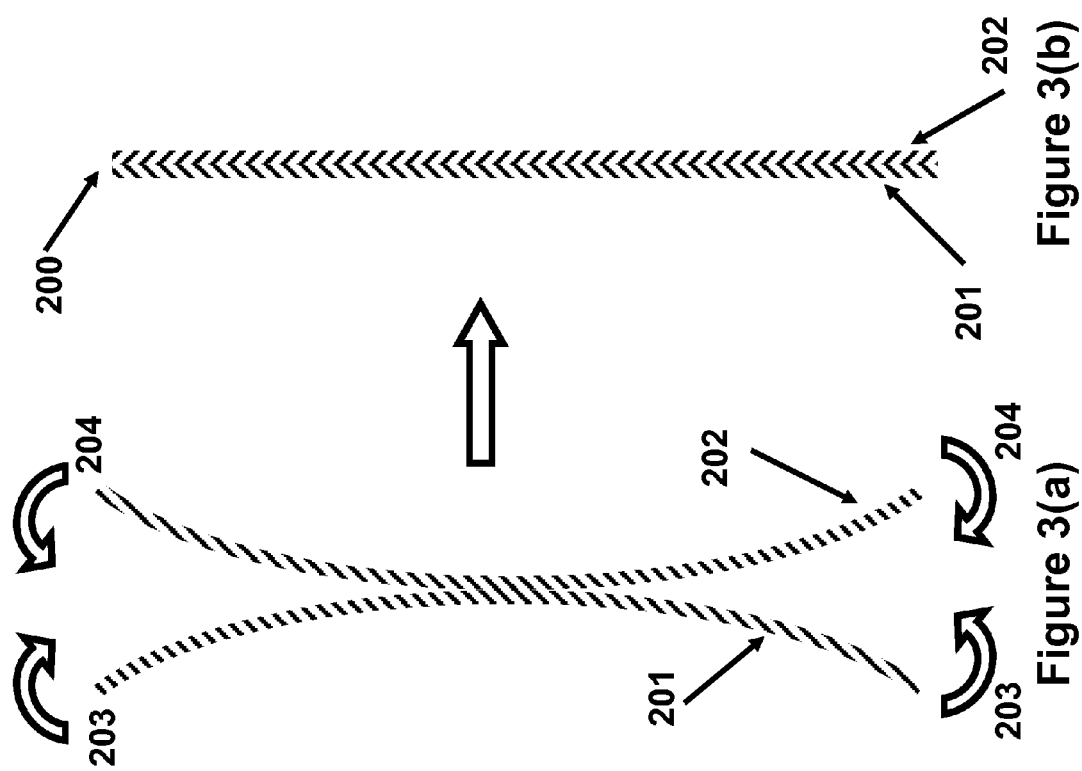

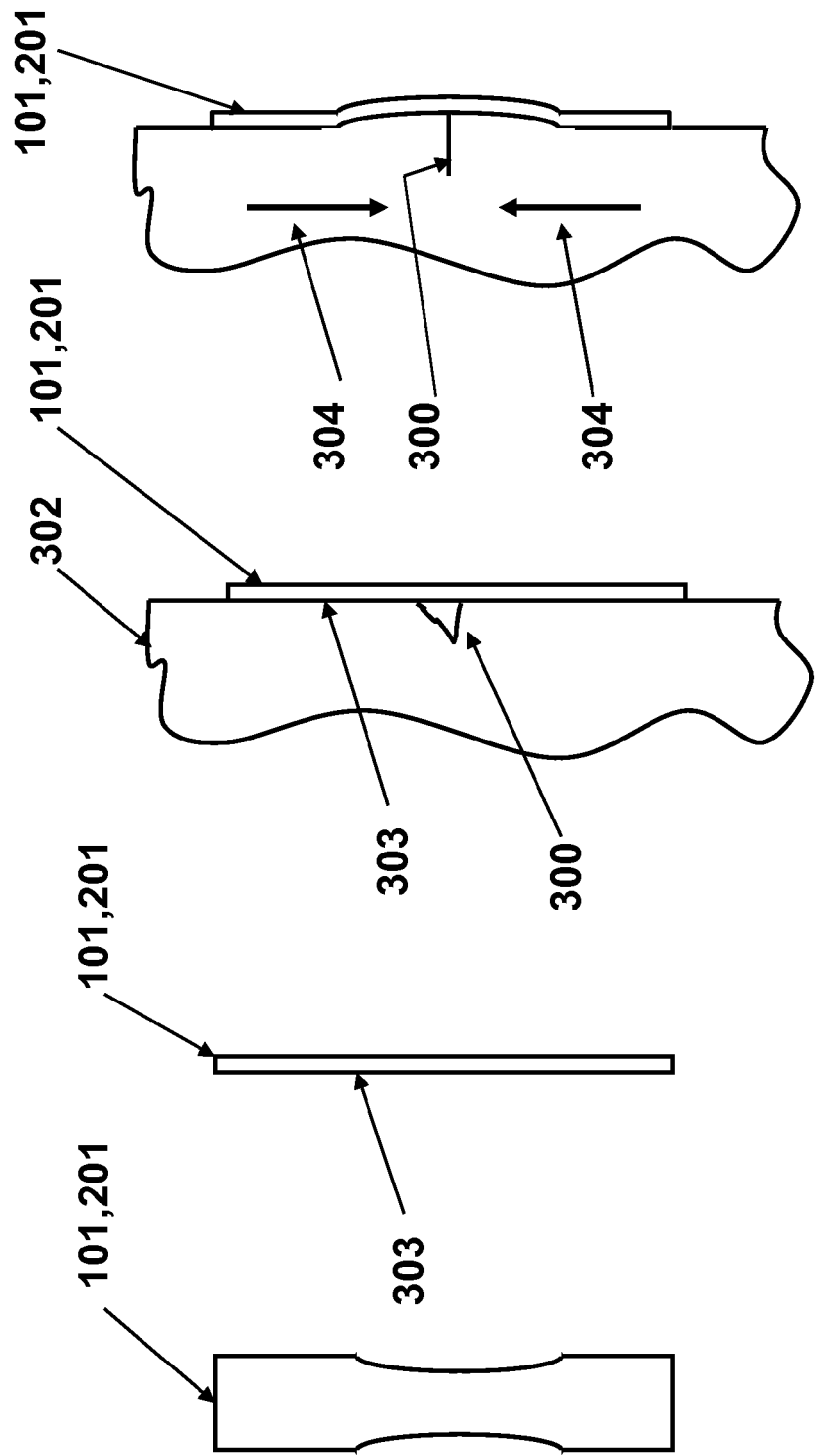

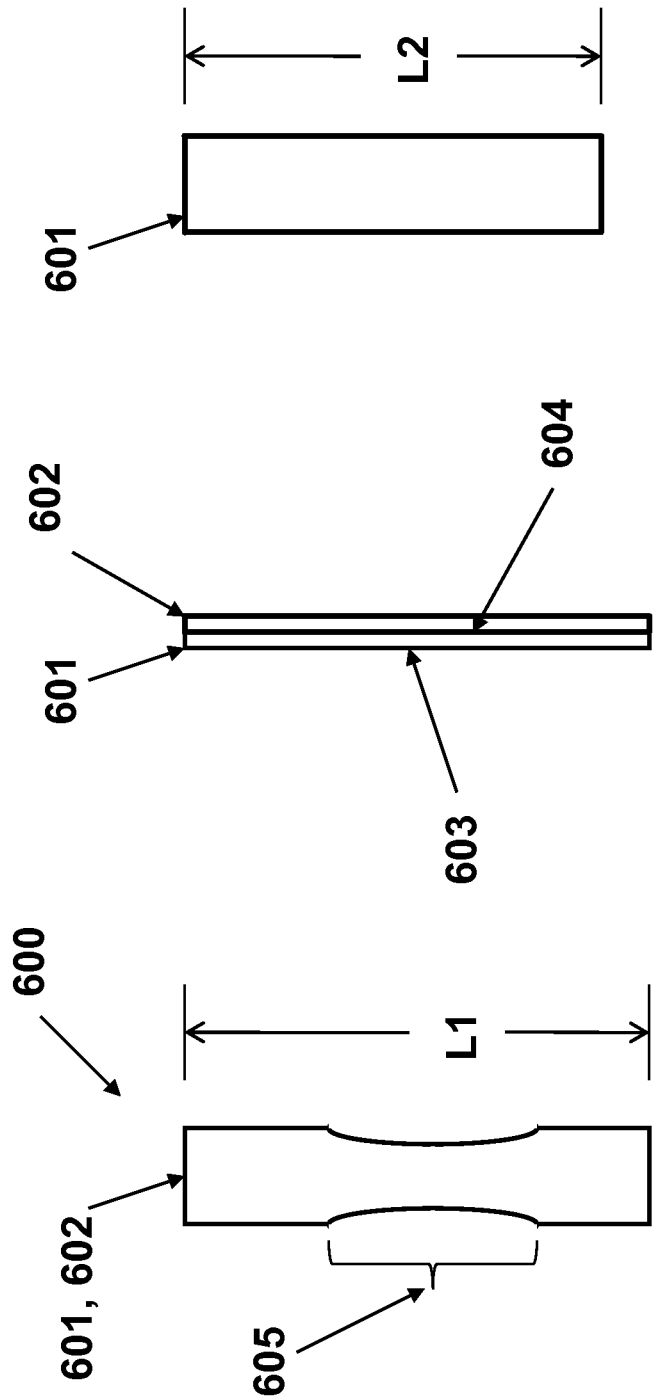

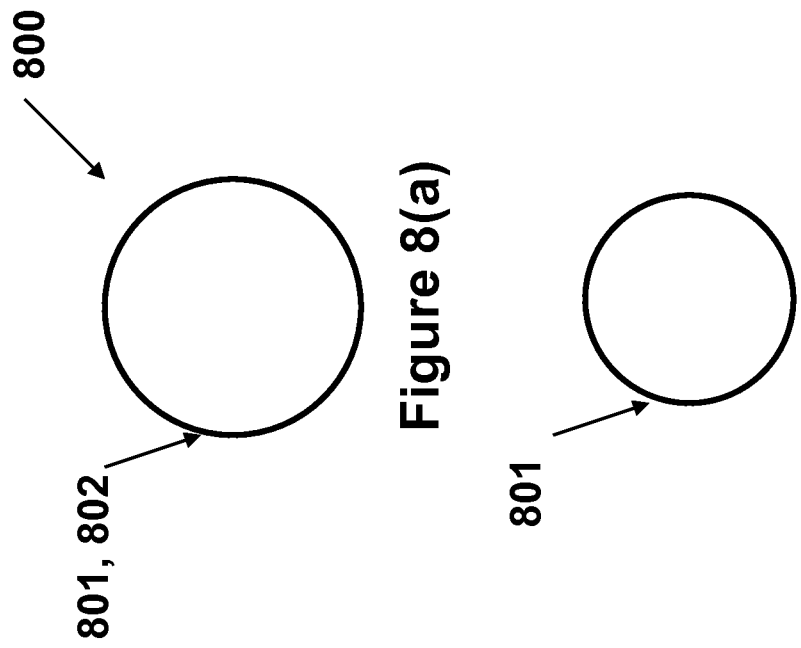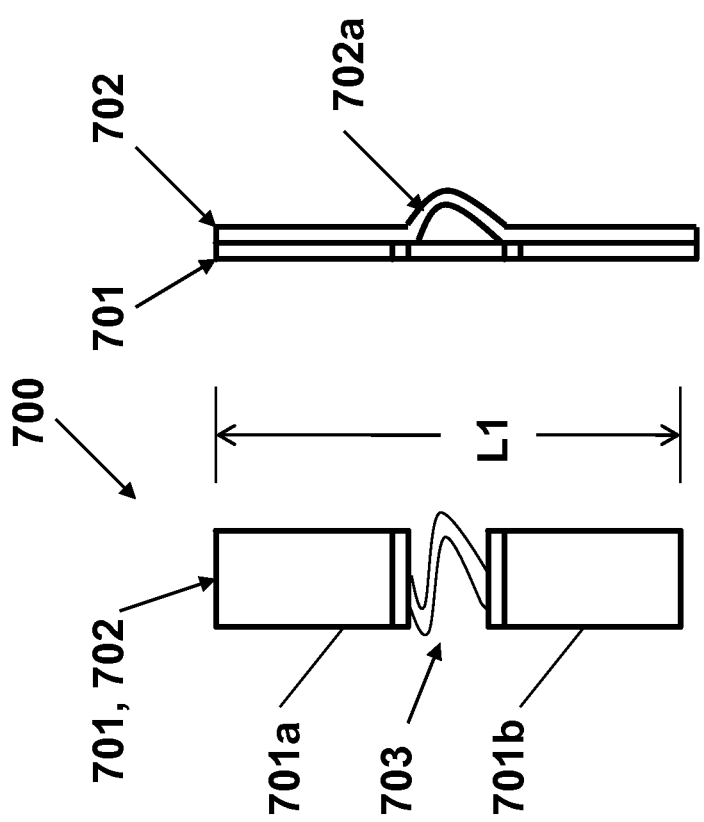

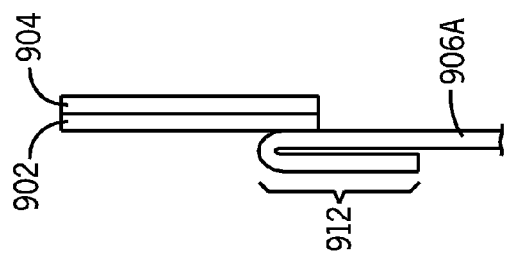
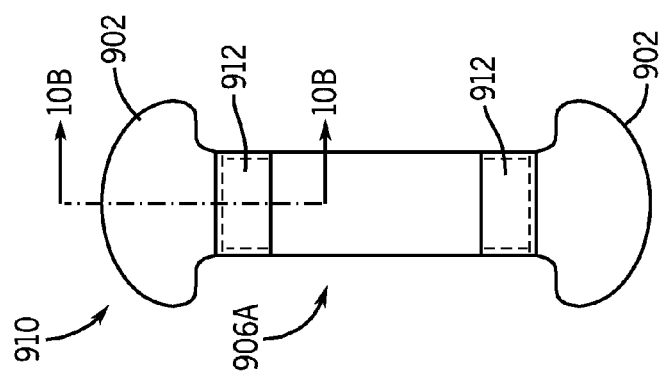
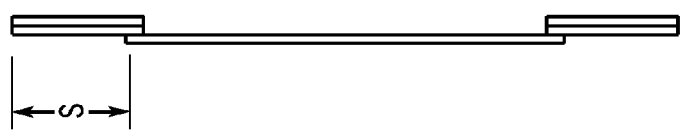
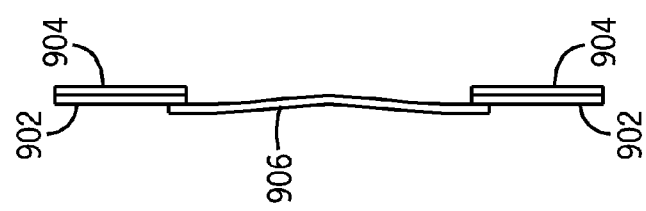
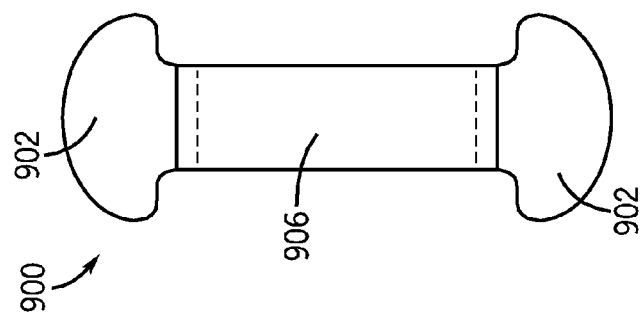

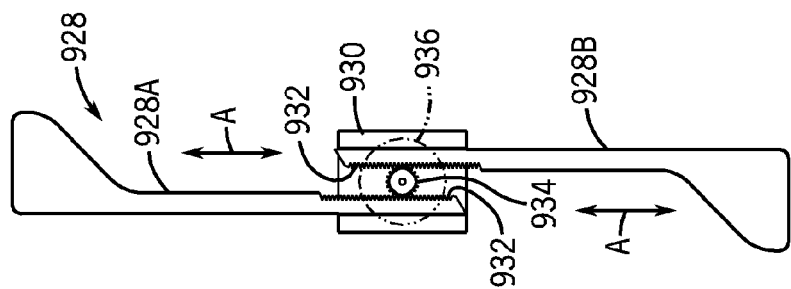
FIG. 12
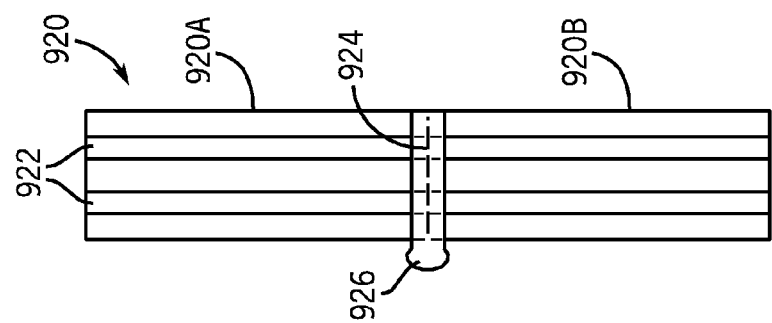
FIG. 11
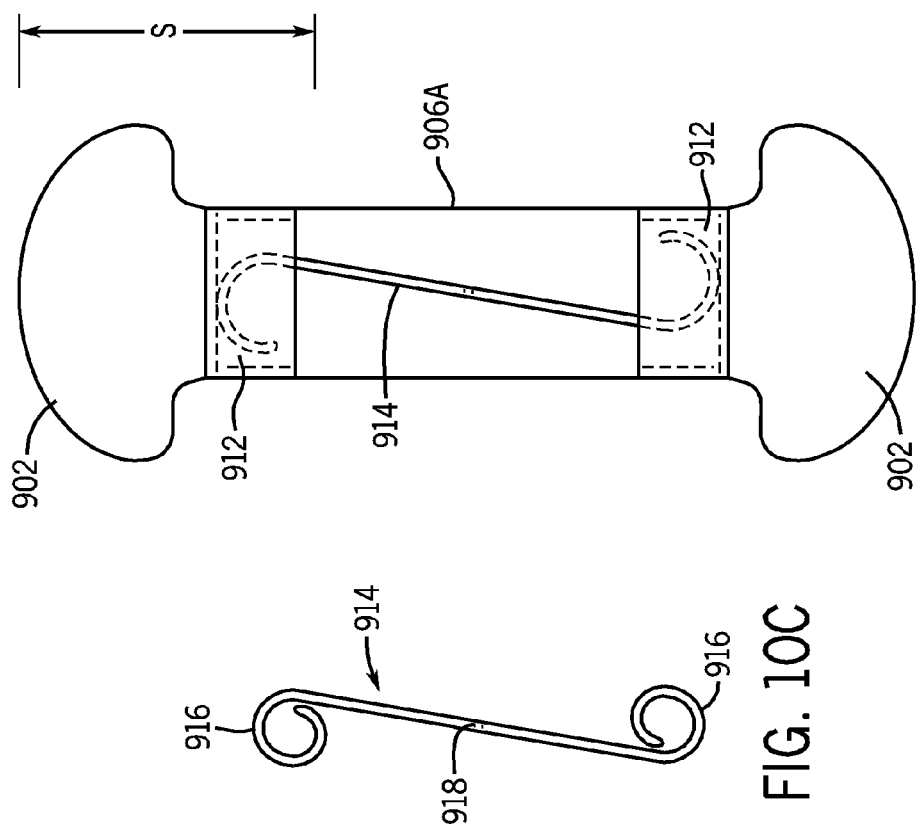
FIG. 10D
FIG. 10C

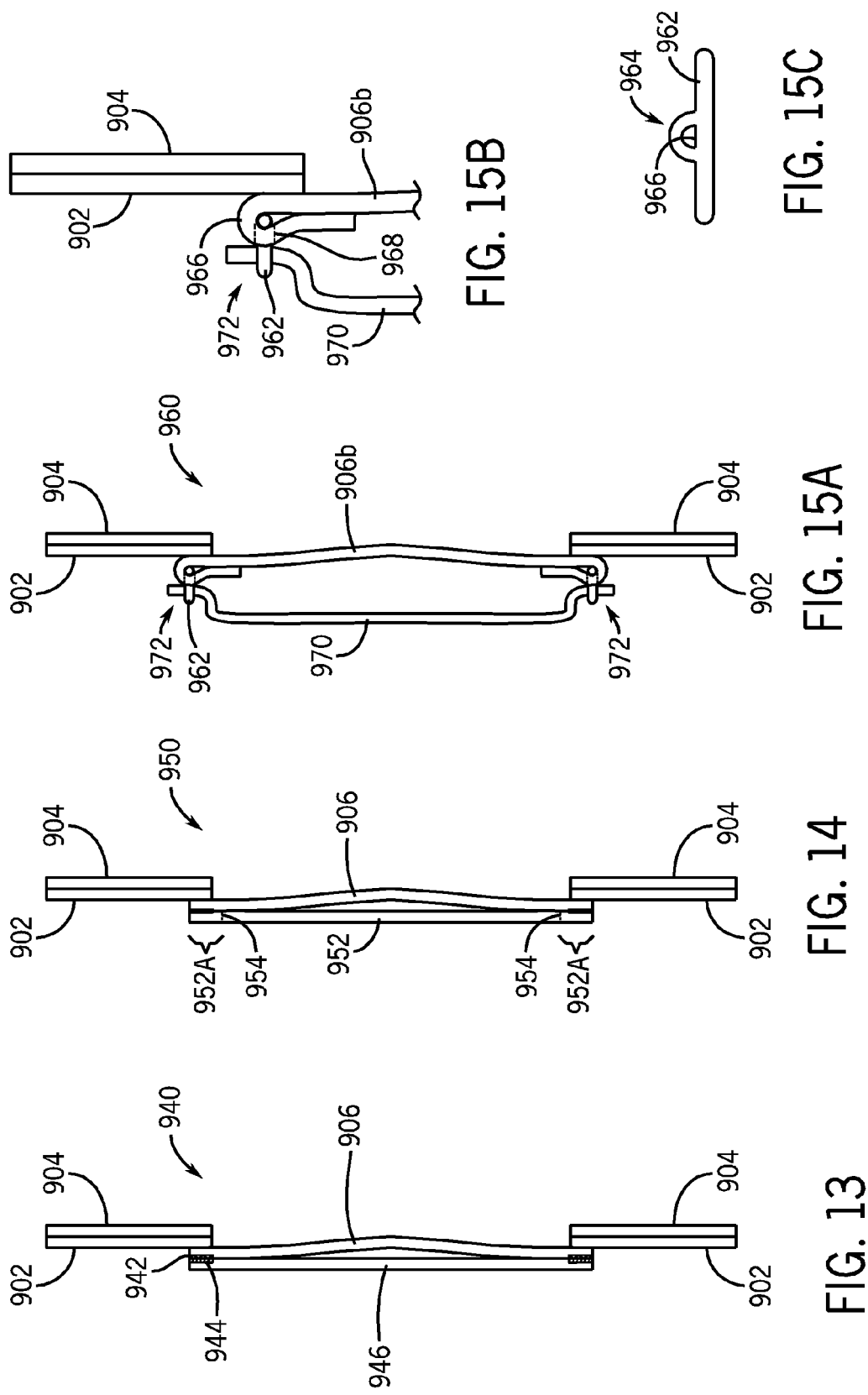

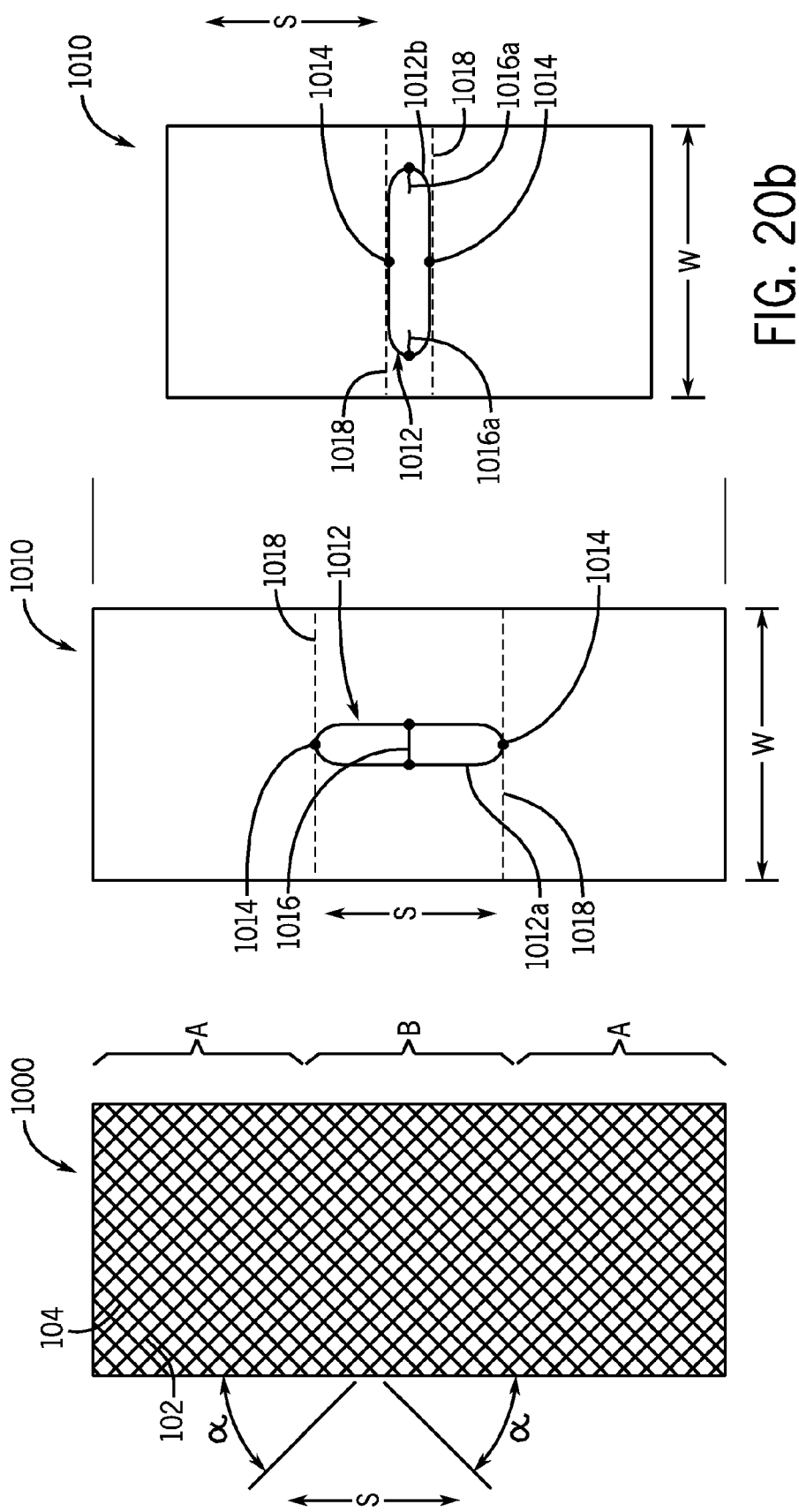

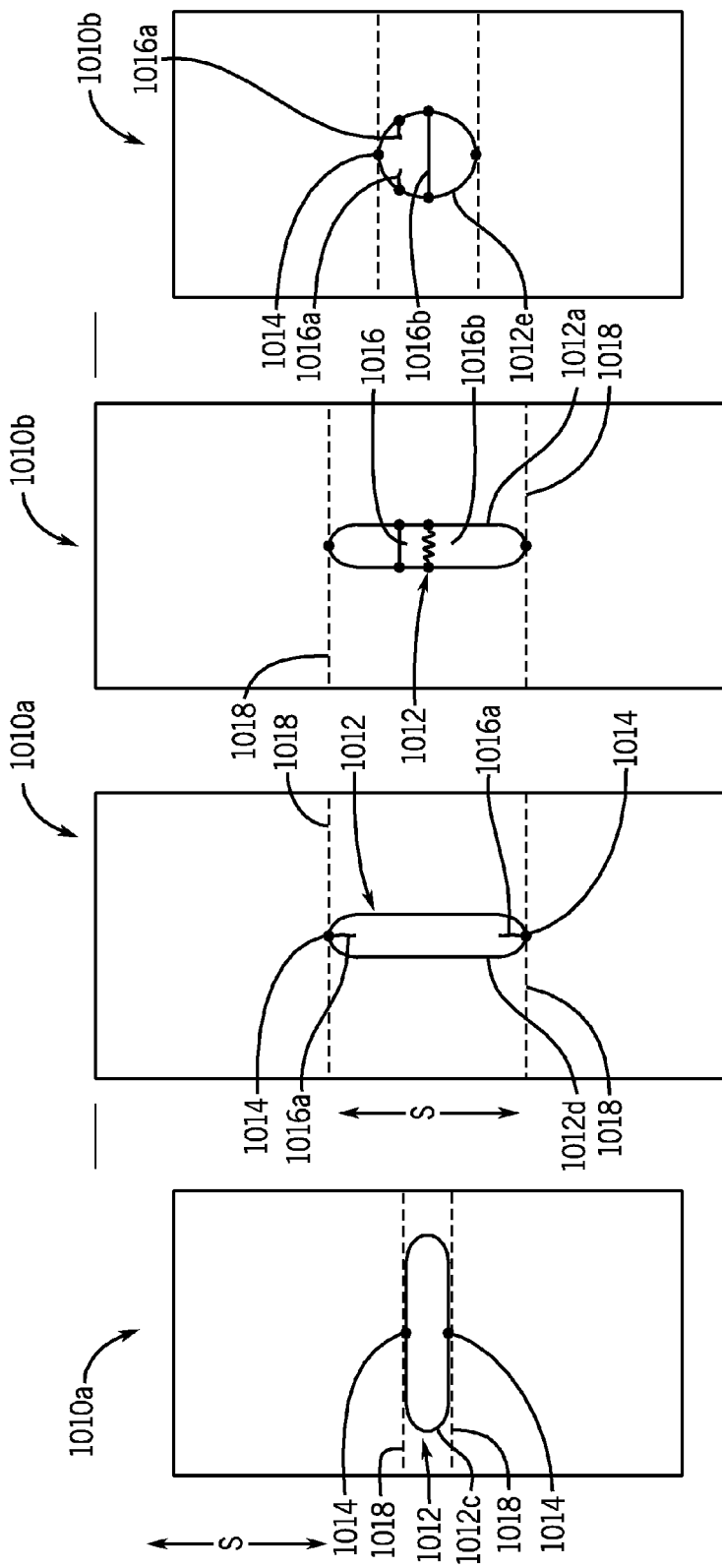

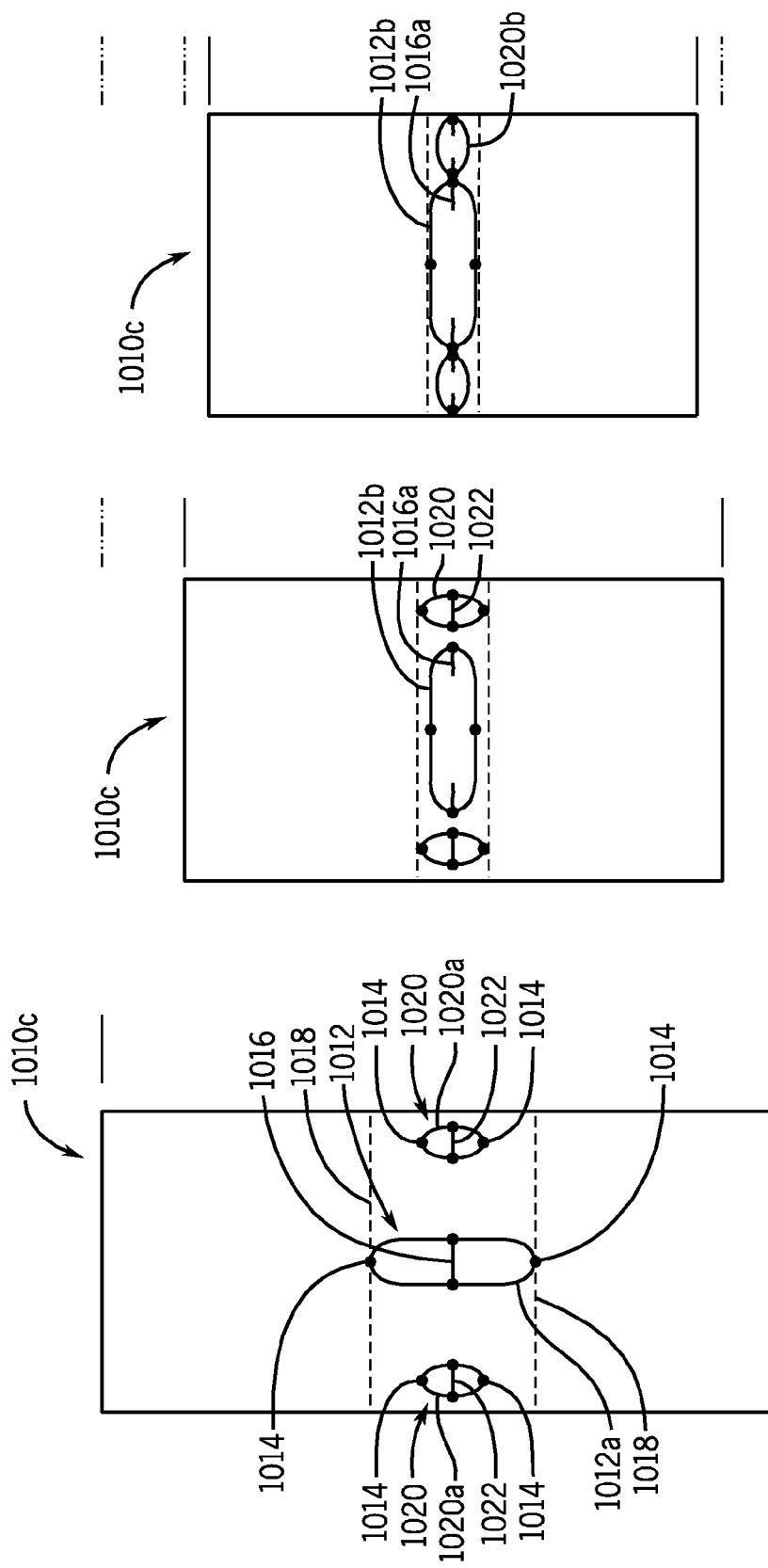

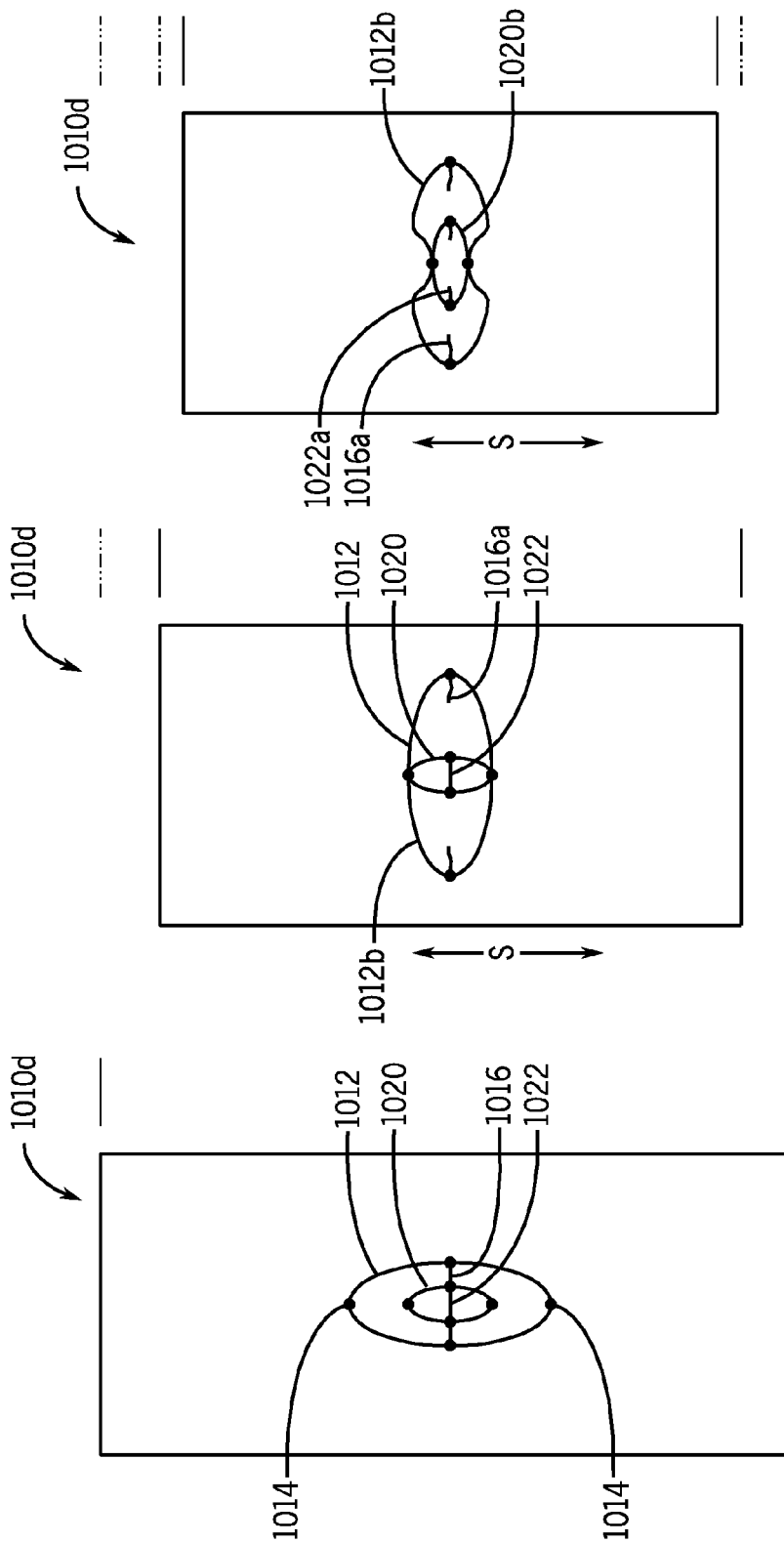

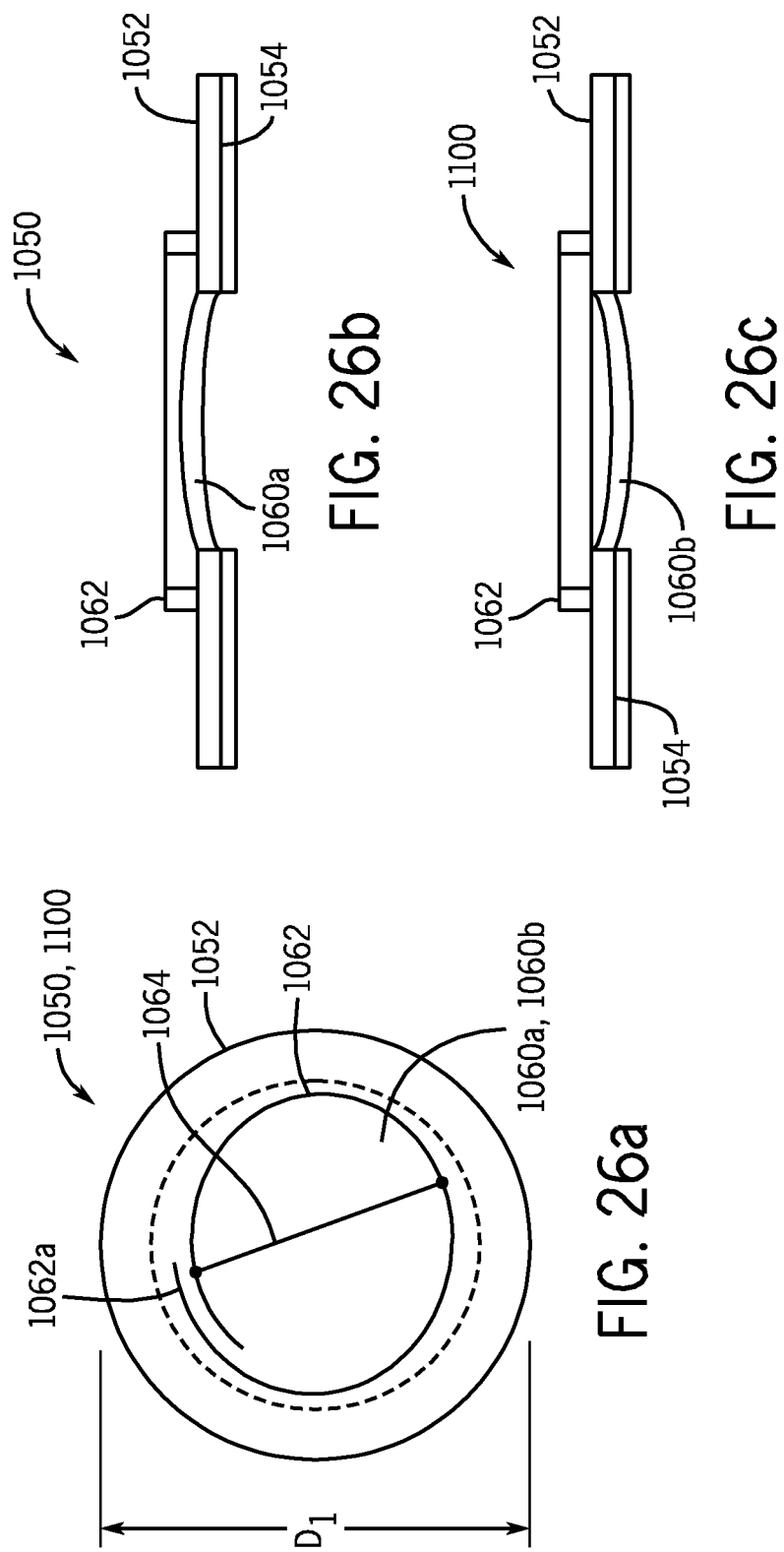

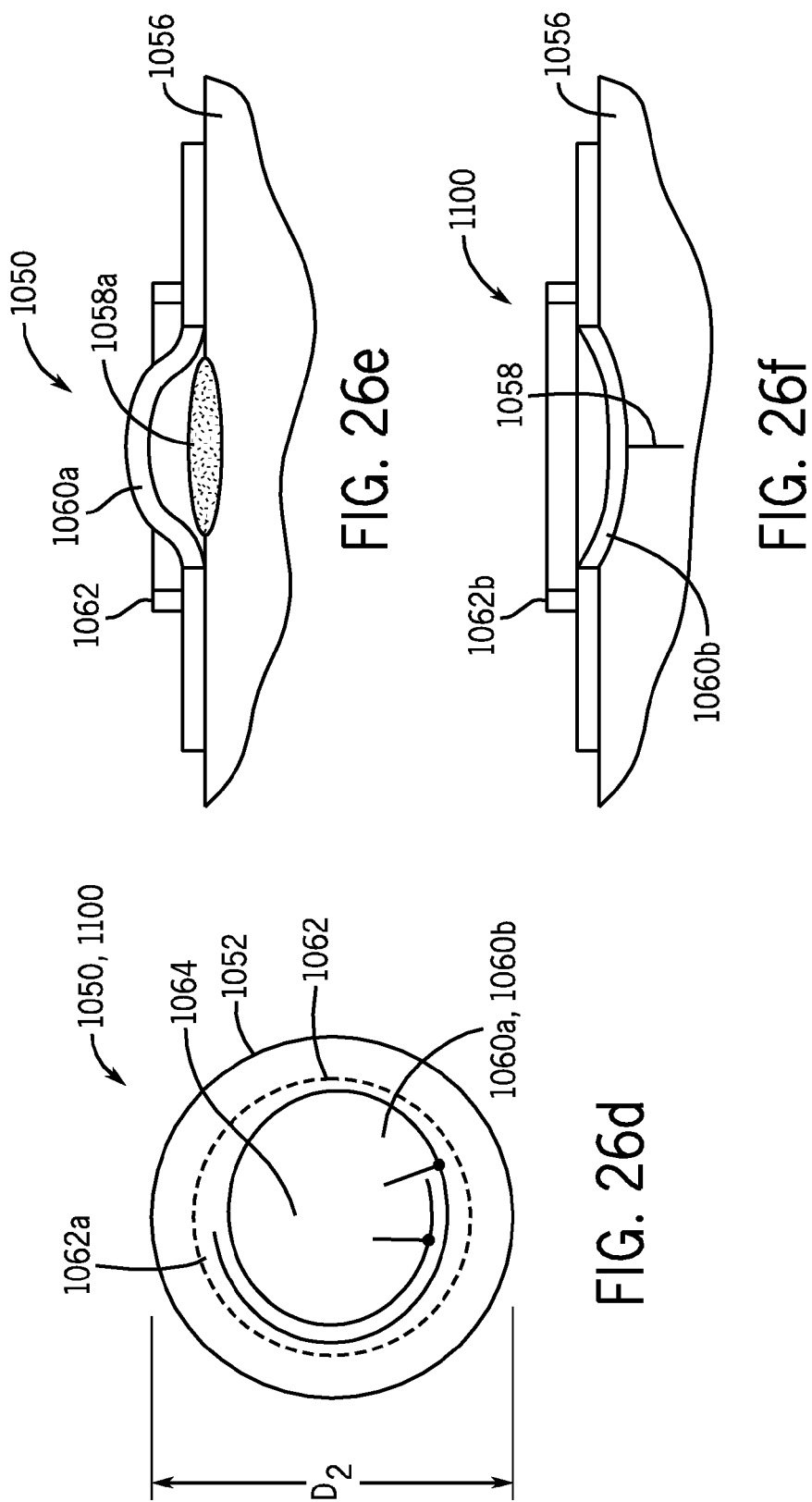

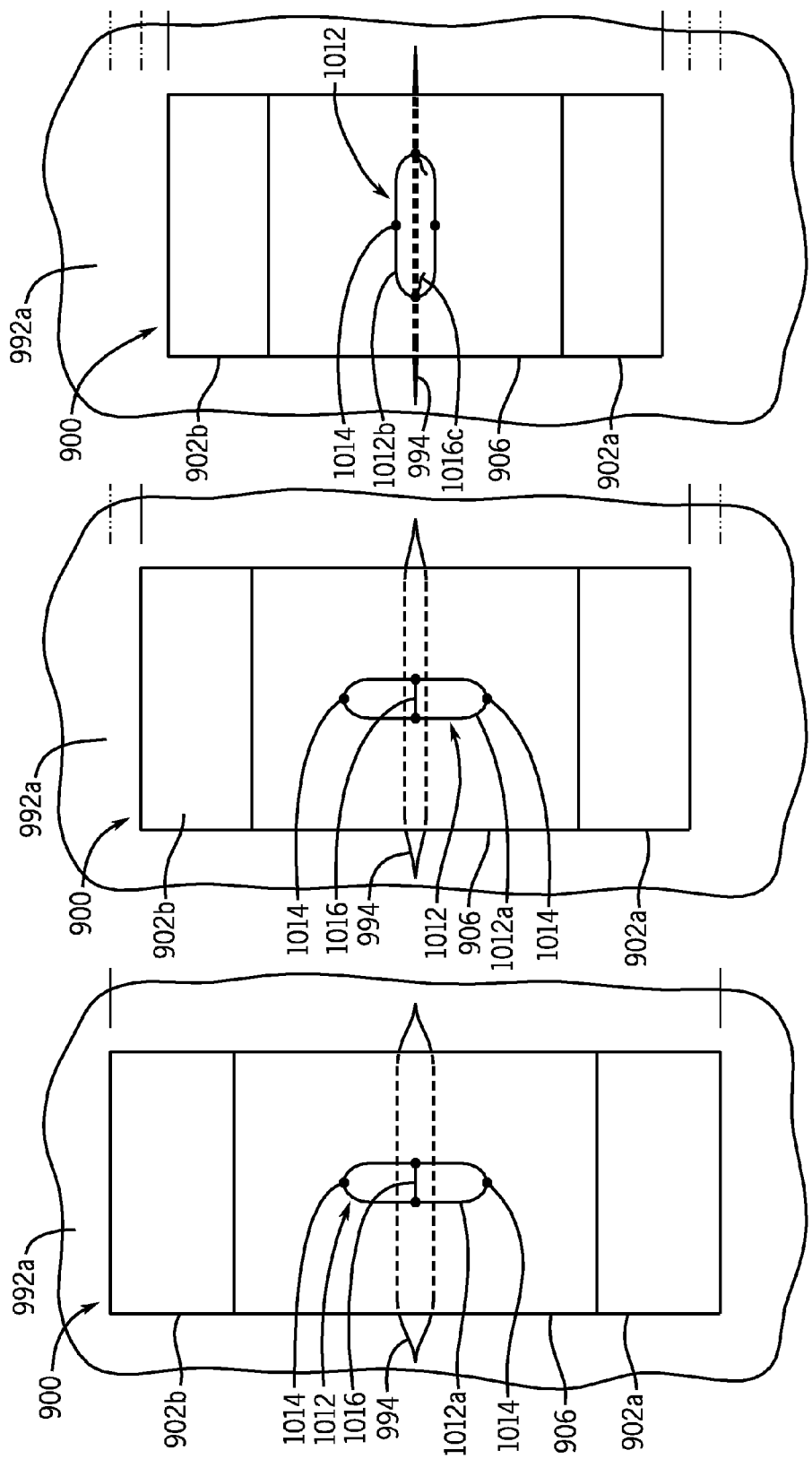

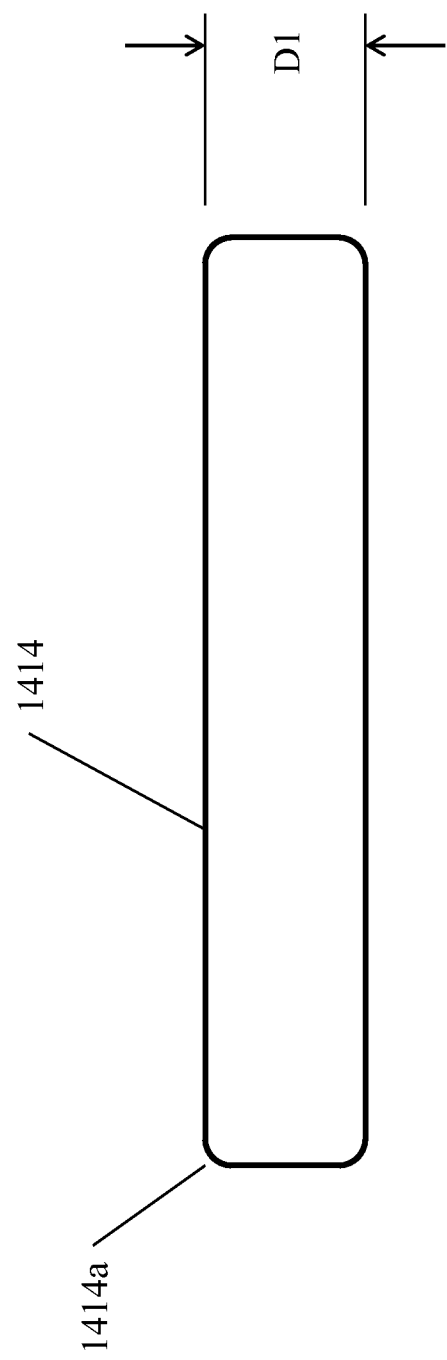

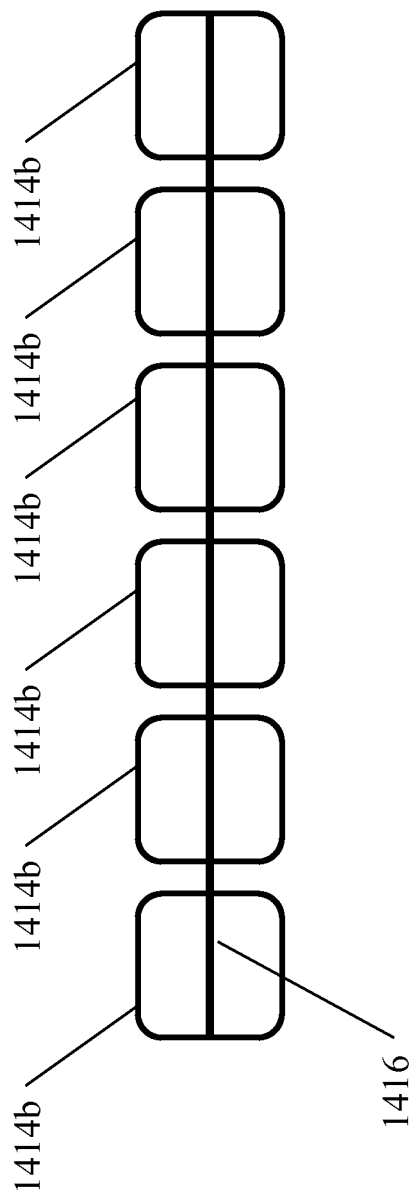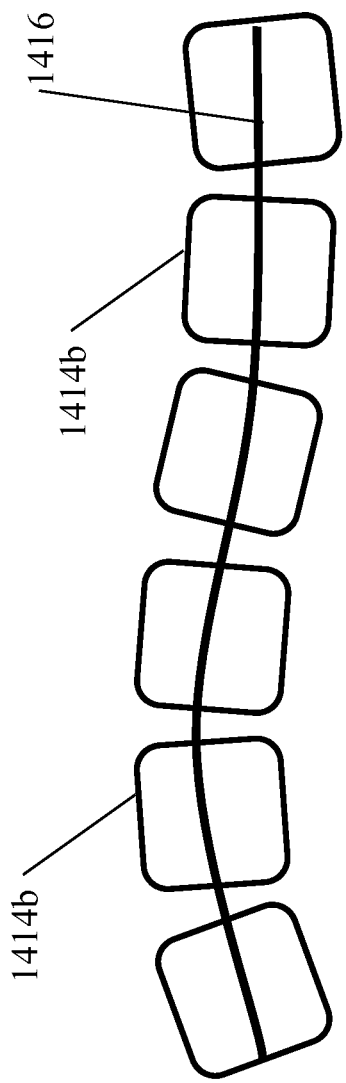

SHAPE AND PRESSURE ADJUSTABLE DRESSING

CROSS-REFERENCE TO RELATED APPLICATION

This application is a continuation-in-part of U.S. application Ser. No. 13/459,246 filed on Apr. 29, 2012, which is a continuation-in-part application of U.S. application Ser. No. 13/230,797 filed on Sep. 12, 2011, which is a continuation-in-part application of U.S. application Ser. No. 13/046,767 filed on Mar. 13, 2011, which is a continuation-in-part application of U.S. application Ser. No. 12/983,314 filed on Jan. 2, 2011, the contents of each of which is incorporated herein by reference.

BACKGROUND

1. Field of the Invention

The present invention relates generally to dressings, and more specifically to shape and pressure adjustable dressings.

2. Prior Art

In many situations, dressings are desired to apply a certain amount of pressure on a wound or to apply a certain amount of force to close a wound or keep it closed, even over time as inflammation subsides. In other situations, it may be desired to increase the pressure or force over time to assist healing without a change in the dressing. In yet other situations it may be desirable to vary the pressure or force distribution over time. However, the currently available materials used for dressing wounds are difficult if not impossible to be used to achieve the above results in general, and to achieve it with ease and in a reliable manner in particular, even with the use of such aids as elastic components or tension fixtures.

In other situations, the dressing may be required to cover certain surfaces over the body that due to the shape of the surfaces, it may be difficult to make a close fit and even more difficult to apply pressure to the surface and sustain the applied pressure over time. In such situations, the dressing has to not only conform to the covered surfaces, but at the same time may have to provide a certain pattern of pressure or force to achieve certain goals.

A need therefore exists for a method to construct dressings that can be readily applied to the desired area, and then have the capability of its shape to be varied and/or apply a desired pattern of pressure or force to the covered area. The disclosed methods of varying the shape of the component just before use, is also advantageous in many applications since it can be used to reduce the size of the required packaging, e.g., a blister shaped component may be initially stored as a relatively flat sheet and then be turned to a blister just before application to the patient's skin.

SUMMARY

Accordingly, a dressing for application to skin is provided. The dressing comprising: first and second portions; an adhesive applied on a surface of the first and second portions for adhering the first and second portions to the skin; an elastic member having one end connected to the first portion and another end connected to the second portion, the elastic member having portions defining a pocket; and a locking member disposed in the pocket for restraining the elastic member into a first shape; wherein when the locking member is at least partially removed from the pocket, the elastic member moves in a direction towards an unrestrained second shape.

The locking member can comprise two or more locking members, each having a different dimension in the direction.

The locking member can be formed of a series of locking members connected by a flexible member. The dressing flexible member can be one of a string or fabric.

The locking member can be rectangular in shape and has rounded corners.

The elastic member can be formed in a loop shape. The elastic member and first and second portions can be formed separately and connected together with the elastic portion being disposed between the first and second portions. The elastic member and first and second portions can be integrally formed in a single piece, such as by being woven in the single piece, in which case, only the elastic portion of the single piece can be woven with elastic fibers in the direction.

Also provided is a dressing for application to skin. The dressing comprising: first and second portions; an adhesive applied on a surface of the first and second portions for adhering the first and second portions to the skin; an elastic member connecting the first and second portions; a locking member connecting the first and second portions to restrain the elastic member into a first shape; weakened portions disposed between the locking member and each of the first and second portions for facilitating removal of the locking member from connecting the first and second portions; wherein when the locking member is removed from connecting the first and second portions, the elastic member moves in a direction towards an unrestrained second shape.

The weakened portions can comprise a plurality of perforations.

The locking member can comprise a projection disposed on at least one end for grasping by a user.

Still further provided is a method of closing a wound with a dressing. The method comprising: restraining at least a portion of the dressing corresponding to the wound into a first shape; adhering first and second portions of the dressing across the wound; removing the restraint from the dressing while the first and second portions are adhered to the skin by removing a member from the dressing to allow at least the portion to move towards a second shape and apply a force tending to close the wound.

The portion of the dressing can be a material having elasticity in at least a direction across the wound. The material can comprise one or more layers. Where the material comprises two layers, the material can be formed in a loop shape. The loop shape material can be formed in a single woven piece with the first and second portions, in which case the single piece can be woven with only the loop portion having elastic fibers in a direction tending to close the wound.

The removing can comprise removing the member from a pocket formed in the portion.

The removing can comprise removing the member along weakened portions formed between the member and the first and second portions.

The removing can comprise removing the restraint in discreet steps.

BRIEF DESCRIPTION OF THE DRAWINGS

These and other features, aspects, and advantages of the apparatus and methods of the present invention will become better understood with regard to the following description, appended claims, and accompanying drawings where:

FIG. 1(a) illustrates a first embodiment of a dressing having a first layer and a second layer.

FIG. 1(b) illustrates the dressing of FIG. 1(a) in which the first and second layers are separated.

FIG. 1(c) illustrates the first layer of FIG. 1(b) after the second layer has been separated therefrom.

FIG. 2(a) illustrates the dressing of FIG. 1(a) attached to the surface of skin.

FIG. 2(b) illustrates the dressing of FIG. 2(a) after the second layer has been removed.

FIG. 3(a) illustrates two component sheets of a second embodiment of a dressing.

FIG. 3(b) illustrates the two component sheets of FIG. 3(a) attached into an assembly.

FIG. 3(c) illustrates one of the components of FIG. 3(b) attached to the skin of a patient and the other of the components separated therefrom.

FIG. 5(a) illustrates a top view of yet another embodiment of a dressing.

FIG. 5(b) illustrates a side view of the dressing of FIG. 5(a) when at a temperature lower than a threshold temperature.

FIG. 5(c) illustrates the dressing of FIGS. 5(a) and 5(b) attached over a cut in skin.

FIG. 5(d) illustrates the dressing of FIG. 5(c) after the dressing has attained a temperature greater than the threshold temperature to close the cut in the skin.

FIG. 6(a) illustrates a top view of yet another embodiment of a dressing.

FIG. 6(b) illustrates a side view of the embodiment of FIG. 6(a).

FIG. 6(c) illustrates the dressing of FIGS. 6(a) and 6(b) after the second layer has been removed.

FIG. 7(a) illustrates a top view of a variation of the embodiment of FIG. 6(a).

FIG. 7(b) illustrates a side view of the embodiment of FIG. 7(a).

FIG. 8(a) illustrates a top view of another variation of the embodiment of FIG. 6(a).

FIG. 8(b) illustrates the dressing of FIG. 8(a) after the second layer has been removed.

FIG. 9 illustrates a top view of yet another embodiment of a dressing

FIGS. 9A and 9B illustrate a side view of the dressing of FIG. 9 in a first shape and second shape, respectively, where the second shape is elongated.

FIG. 10A illustrates a top view of yet another embodiment of a dressing.

FIG. 10B illustrates a partial section view as taken along line 10B-10B in FIG. 10A.

FIG. 10C illustrates a holding member for use in the dressing of FIG. 10A.

FIG. 10D illustrates a top view of the dressing of FIG. 10A held in an elongated shape with the holding member of FIG. 10C.

FIG. 11 illustrates an alternative holding member for use with the dressing of FIG. 10A.

FIG. 12 illustrates another alternative holding member for use with the dressing of FIG. 10A.

FIG. 13 illustrates yet another embodiment of a dressing.

FIG. 14 illustrates yet another embodiment of a dressing.

FIG. 15A illustrates yet another embodiment of a dressing.

FIG. 15B illustrates a partial enlarged view of the dressing of FIG. 15A.

FIG. 15C illustrates a clip used in the dressing of FIG. 15A.

FIG. 19 illustrates an alternative woven portion for a dressing capable of deforming from the second shape into the first shape.

FIGS. 20a and 20b illustrate another alternative dressing portion.

FIGS. 20c and 20d illustrate an alternative of the dressing portion of FIGS. 20a and 20b.

FIGS. 20e and 20f illustrate another alternative of the dressing portion of FIGS. 20a and 20b.

FIGS. 21a-21c illustrate another alternative of the dressing portion of FIGS. 20a and 20b.

FIGS. 22a-22c illustrate an alternative of the dressing portion of FIGS. 21a-21c.

FIGS. 24c and 24d illustrate an alternative dressing portion of FIGS. 25a and 25b.

FIGS. 26a-26f illustrate two additional embodiments of a dressing having utility for puncture wounds.

FIGS. 27a-27c illustrate a variation of the dressing of FIGS. 18a-18c.

FIG. 39 illustrates the locking member of the dressing of FIG. 36.

FIG. 40a illustrates an alternative locking member for use with the dressing of FIG. 36 to facilitate curving the same about an irregular shaped wound.

FIG. 40b illustrates the alternative locking member of FIG. 40a in a curved configuration.

DETAILED DESCRIPTION

Figure 4C:
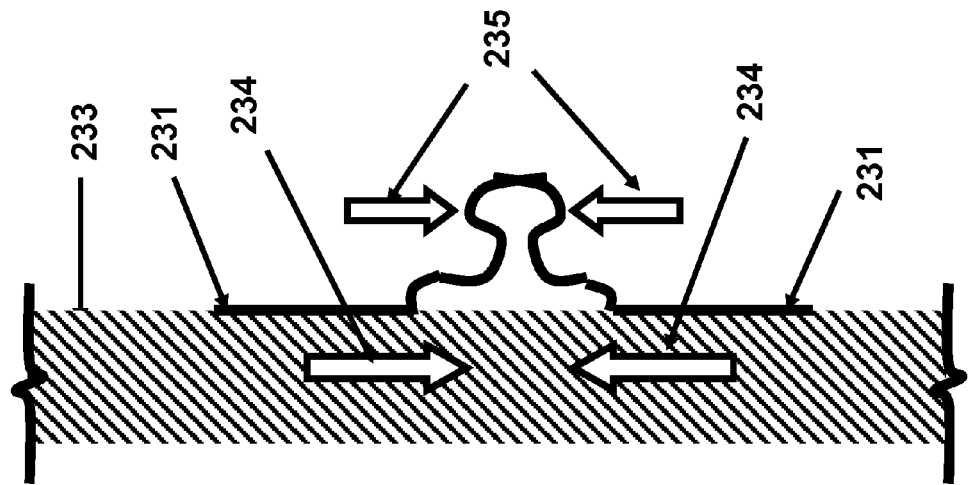
FIG. 4(c) illustrates the dressing of FIG. 4(b) being compressed together.

A schematic of a basic design based on a first embodiment is shown in the FIGS. 1(a) to 1(c). In FIG. 1(a), the cross-section of a plane assembly 100 is shown, and consists of a first layer 101 and a second layer 107. The two layers are attached together using any methods known in the art, such as with adhesives, so that the user could readily separate them. The layer 101 consists of components 102 and 104, which are attached together with an intermediate component 103. Similarly, the components 104 and 106 are attached together with an intermediate component 105. The components 102, 104 and 106 are considered to be relatively devoid of internal stresses, while the components 103 and 105 have been originally shaped as shown in FIG. 1(c), but have been elastically flattened and held in the flattened configuration by the component 107, as shown in FIG. 1a, to form the assembly 100. Obviously, if the component (layer) 107 is separated from the assembly 100, as shown in FIG. 1(b), the components 103 and 105 would return to their original shape, and the layer 100 will take the shape shown in FIG. 1(c).

The first layer 101 can be formed of any material which can be fabricated into a certain (original) shape and elastically deformed into another shape, such as a plastic or metal or combination thereof. Furthermore, plate 107 can be formed of any material rigid enough to prevent the first layer 101 from taking the original shape while attached to the first layer.

In the schematic of FIGS. 1(a)-1(c), the assembly 100 is shown to be in the shape of a flat plate. It is, however, appreciated by those skilled in the art, that the assembly may form a curved surface; more stressed (preloaded or elastically deformed) and essentially unstressed (preloaded or elastically deformed) components may be used in the assembly; and in their unstressed state, the stressed (preloaded or elastically deformed) component(s) may have been constructed to assume a variety of shapes (configurations), including complex shapes and curvatures. In general, upon the removal of the constraining component(s), the stressed (preloaded or elastically deformed) component(s) will tend to return to their unstressed (natural) state. It is appreciated that the stressed component(s), while tending to return to their unstressed (natural) state (shape or configuration), may still retain part of their induced internal stresses.

The dressing assembly 100 may be applied to the body surface 110, e.g., via an adhesive layer on the free surface of the layer 101 (not shown), as can be seen in FIG. 2(a). Once the assembly 100 is securely attached to the body surface, the layer 107 (wholly or partially) is removed. FIG. 2(b) shows the case in which the layer 107 is removed. At least part of the preloading stresses in the components 103 and 105 are then released. As a result, the layer 101 tends to its natural (stress-free) state. The components 102 and 106 are then pulled towards each other in the direction 112, and the underlying skin is pulled together. Thereby if a cut was present in the section of the skin 111 between the 102 and 106 components, the above action would tend to force it closed. The component 104 of the layer 107 is also pushed away from the skin.

In the schematics of FIGS. 1(a)-1(c), for the sake of simplicity, only two distinct layers are used and only one of the layers is provided with the preloaded components. However, more than one layer can be utilized, and layers with partially preloaded components may also be used to construct the dressing components. It is also possible to construct devices that are constructed with at least two layers of fully preloaded components. In addition, the final assembly (assembly 100) does not have to be flat, and may assume any appropriate shape and configuration as dictated with the particular application.

It should also be noted that in the schematics of FIGS. 1(a)-1(c), and in the remaining illustrations, only living joints are illustrated at discontinuities in the first layer 101. It is, however, appreciated that regular joints, such as pin joints and/or sliding joints, may also be used in the construction of the present devices.

Another embodiment of a dressing is shown schematically in FIGS. 3(a)-3(c). The dressing assembly 200 shown in FIG. 3(b), consists of at least two components (sheets) 201 and 202, which in their free (natural) form are curved as shown in FIG. 3(a). The dressing 200 is assembled by deforming the components 201 and 202 to their assembly configuration and attaching them together, preferably using adhesives, to achieve their final (assembled) configuration. In FIG. 3(a), and for the sake of simplicity, the two components 201 and 202 are shown to be deformed in a symmetrical manner, which upon bending in the directions 203 and 204, respectively, could be nearly flattened to their final shape in the assembly. In this particular case, since the two components 201 and 202 are considered to be identical and with symmetrical initial deformation, then upon their assembly after being flattened would assume a flat configuration. It is readily seen that by using two or more components with varying shape, and/or size, and/or materials, and/or initial (free or natural) configuration, one could construct infinite number of assemblies, which upon partial or full removal of one or more of the components, the desired final shape, size, configuration, and when appropriate applied force (moment or torque) to the attached member, could be achieved.

In certain assemblies, it may be necessary to use less strong adhesives for assembling certain components of the assembly for reasons such as ease of removal. In such cases, it may be necessary to provide mechanical locking action, such as by bending sides or corners of one component over the other, or by using attachment methods such as sewing or stapling or by using one or more clipping elements, etc., which is/are readily removable before applying the dressing to the patient or following its application. FIG. 3(c) illustrates the dressing 200 attached to a surface of the skin and sheet 202 removed, in which case sheet 201 is deformed towards its original shape and the skin takes the shape of the sheet 201 and is pulled together.

Figure 4B:
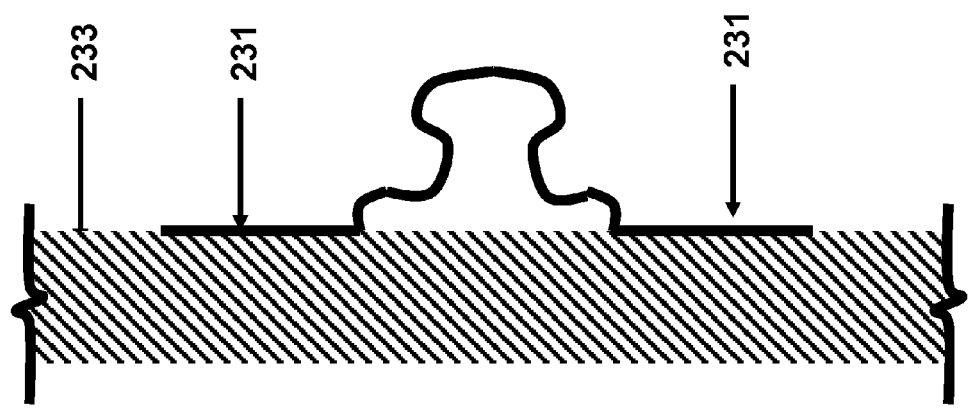
FIG. 4(b) illustrates the dressing of FIG. 4(a) attached to skin of a patient.
Figure 4A:
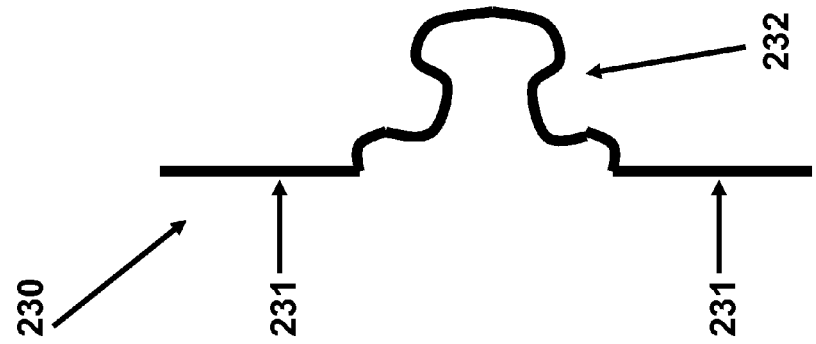
FIG. 4(a) illustrates another embodiment of a dressing.

Yet another embodiment of a dressing is shown in FIGS. 4(a)-4(c). The schematic of the side view of a plate formed with two flat sides 231 and a middle side 232, forming a simple example of a dressing element 230 is shown in FIG. 4(a). The adhesives that are preferably provided on these surfaces may then apply the dressing element 230 to the surface of the skin 233 as shown in FIG. 4(b), via the surfaces 231. The part 232 is then compressed together (or twisted or otherwise deformed) in the direction of bringing the surfaces 231 together (direction 235), such as with a tie-wrap, string wire or the like. As a result, the underlying skin is pulled together in the direction 234, thereby closing a wound or providing a desired compressive pressure, or in short the desired effect.

In all the disclosed embodiments, appropriate dressing components such as gauzes, medications, etc., may be disposed (preferably in the middle regions) of the dressing assemblies to cover the wound. Ventilation or drainage ports may also be provided when appropriate in these regions. Elastic or removable elements may also be provided over or around such regions for administering medication. In certain cases, it may also be desirable to construct one or more components of the assembly with transparent materials so that the affected region could be observed.

In addition, the applied pressure or wound closing action of the dressing element may be increased or decreased over time by removing, e.g., a larger piece of the shape/configuration affecting components or by further deformation of the shape/configuration affecting components. The pressure applied by the dressing can also be varied so that the skin can be "pushed" and "pulled."

Referring now to FIGS. 5(a)-5(d), the component 101, 201 disposed on the skin can be formed, at least in part, of a shape memory material. Thus, when disposed on the skin, the component 101, 201 can change shape, in whole or in part, due to a shape memory effect upon being heated by the temperature of the skin to at or above a transition temperature of the shape memory material. An external heat source may also be used to affect the shape change. Such materials are well known in the art and can be either metals or plastics which exhibit the shape memory effect. A dressing having such a configuration can eliminate the second component 107, 202 since the shape memory material can take one form, such as flat, at a first temperature (FIG. 5(b)) and take another shape, such as that shown in FIG. 5(d) at a second temperature. Thus, the plate 107, 202 is not needed to maintain the sheet 101, 201 in the shape shown in FIGS. 5(a) and 5(b). In this configuration, the dressing component can be shaped as shown in FIG. 5(d) when subjected to a temperature above the threshold temperature (e.g., body temperature) and can be flat when subjected to a temperature lower than the threshold temperature.

This dressing has particular utility when used as a butterfly type dressing for closing wounds that may otherwise require stitches. In this regard, the plan or top view shape of the dressing 101, 201 can be shaped like a conventional butterfly bandage having a narrowed section in the middle thereof, as shown in FIG. 5(a). Once placed over a cut 300 on the skin 302, such as with adhesive on a face 303 of the dressing 101, 201, as shown in FIG. 5(c), preferably disposed on the surface outside of the narrowed portion. After the dressing 101, 201 is warmed by the body heat of the skin, the shape memory material changes its shape to another shape, such as that shown in FIG. 5(d) to close the cut 300 by applying pressure in the direction of arrows 304. The portion of the dressing 101, 201 contacting the cut 300 may have a gauze and/or a medicated layer.

In a variation of such embodiment, the shape memory material dressing can be kept cool and applied to the skin while it is cold. Then the room temperature will activate it to change its shape so that you are not limited to activation with body temperature, which might be very close to the environmental temperature.

Other active materials that could be employed for the dressing could be active polymers, which would require a voltage to get them to pull.

Another embodiment will now be described in which the shape of the dressing changes after release of a release member, similar to those described with regard to FIGS. 1-4, where the shape change is a change in length of the dressing. FIG. 6(a) illustrates a dressing for a wound, generally referred to by reference numeral 600. The dressing 600 includes a first component 601, which can be a first layer, having a first shape with a first length L1. The dressing 600 further includes a second component, which can be a second layer, which is releasably attached to a first surface 604 of the first component 601 to maintain the first component 601 in a second shape different from the first shape. In the embodiment of FIGS. 6(a)-6(c), the second shape has a second length L2 which is longer than the first length. An adhesive is disposed on a surface 603 of the first component 601 different from the first surface 604 for attaching the first component 601 to the wound such that the second component 602 can be released from the first component 601 to allow the first component to take the first shape to apply a pressure to portions of the skin surrounding the wound to close the wound.

Thus, the dressing 600 is applied to the skin by adhering the surface 603 to the skin while the first component 601 is constrained into the first shape have a length L1. The second component 601 is then removed from the first component 601 to remove such constraint and allow the first component 601 to take the second shape having a shorter length L2, thus applying pressure to the skin which tends to close a wound.

The first component 601 can be formed of any material which can be fabricated into the first shape and elastically deformed into the second shape, such as an elastic material which can elastically stretch in at least one direction. Furthermore, the second component 602 can be formed of any material rigid enough to prevent the first component 601 from taking the second shape while attached to the first component 601.

In addition to an elastic material, the change of shape from the first length L1 to the second length L2 can be achieved by any other means for elastically biasing the first component 601 into the first length L1, such as one or more elastically deformed members attached at one end to a first portion of the first component and attached at a second (or another end) to a second portion of the first component. An example of such, referred to by reference numeral 700, is illustrated in FIGS. 7(a) and 7(b) having a biasing member 703 attaching first and second portions 701a, 701b of the first component 701. Such biasing member 703 can be of any material, such as plastic or metal that can elastically deform into the first shape and back to the second shape. FIG. 7(b) illustrates the second component 702 having a loop portion 702a adjacent to the biasing member 703 for facilitating removal of the second component.

The first component can have such elastic properties throughout the length L1 or a portion thereof, such as portion 605 which is adjacent to the wound. Also, although the embodiment of FIGS. 6(a)-6(c) is described with regard to a shape change in one direction, such shape change can occur in a different direction (such as perpendicular to the direction shown) or in more than one direction (such as in the direction shown and a direction perpendicular thereto). An example of such is shown in FIGS. 8(a) and 8(b), referred to by reference numeral 800, in which the first shape of the first component is a first diameter (shown in FIG. 8(a)) and the second shape is a second diameter smaller than the first diameter (shown in FIG. 8(b)). Such a variation is useful to apply pressure to the skin in more than one direction to close a wound, such as a puncture wound.

As discussed above, the first component can further include one or more of a medicament and gauze. As also discussed above, the two components can be attached together using any methods known in the art, such as with adhesives, so that the user could readily separate them and more intermediate components (not shown) can be used.

Another embodiment of a shape and/or pressing adjustable dressing will now be described with regard to FIGS. 9, 9A and 9B, referred to generally with reference numeral 900. The dressing 900 includes adhesive portions 902 at each end of the dressing 900 having an adhesive for adhering to skin and a release layer 904 which is releasably adhered to the adhesive portions such that it can be removed when the adhesive portions are to be adhered to the skin. The dressing further includes a portion 906 capable of being elastically deformed from a first shape to a second shape. As discussed above, the change in shape can take a great number of forms, such as being elongated, as shown in FIG. 9B (stretched by "S"). In the case where portion 906 changes shape by elongating, the same can facilitate such elongation with biasing elements or elastic material. The adhesive portions 902 and portions 906 can be connected together by sewing, adhering, heat welding and the like. Further, although the adhesive portions 902 and portion 906 are illustrated as separate portions, the same can be integrally formed. As will be described below, the dressing 906, and variations thereof, can be used to close a wound by itself (see FIGS. 18A-18C) or with various holding members, examples of which are described below (see FIGS. 10A-16B). The holding member has been referred to alternatively above as a second component and the adhesive portions 902 and portions 906 as a first component.

FIGS. 10A and 10B illustrate a first variation of the dressing 900 of FIG. 9 in which the dressing is used together with a holding member. The dressing, generally referred to by reference numeral 910, is similar to that of the dressing in FIG. 9 in which like reference numerals refer to similar features, except that a pocket 912 is formed at each of two ends of the portion 906A. The pocket 912, as shown in FIG. 10B can be formed by folding over an end of the portion 906A on itself and closing the same to form a pocket 912, by sewing, adhering, heat welding or the like.

FIG. 10C illustrates a holding member 914 which can take any number of shapes, such as having curved ends 916 and a weakened portion 918. The length of the holding member is such that when the curved ends 916 are disposed in the pockets 912, the portion 906A changes shape by elongating a distance "S". The holding member 914 can be formed of many materials, such as wire, plastic and the like as long as it is rigid enough to maintain the portion 906A in the elongated state and may also be flexible such that the holding member and dressing can be applied over a curved surface of the skin. Although shown elongated flat, the holding member can also maintain the portion 906A elongated in a non-linear shape, such as curved.

As discussed above, the dressing 910 can be applied to the skin in the elongated state by removing the release layers 904 and adhering the dressing to the skin about the wound. After application to the skin, the holding member 914 can be removed or released such that the portion 906A can return to or towards its first shape. Such can be achieved by simply removing the holding member 914 from the pockets 912 or cutting or breaking the holding member 914, such as with a weakened portion 918. Such weakened portions are well known in the art and can include a perforated area or reduced cross-section area.

As shown in FIG. 11, the holding member can also be a thin member 920 which can have one or more ribs 922 for added rigidity. The thin member can be formed of any material such as plastic. The thin member 920 can be simply removed from the pockets 912 or cut or broken, such as with a weakened portion 924. The weakened portion 924 can be as described above, and may also be realized by forming the thin member of two pieces 920A, 920B and holding the same together with tape 926 or other retaining means. When the dressing is desired to change to or towards its first shape (e.g., un-elongated), the tape is simply removed and the two resulting pieces 920A, 920B of the holding member 920 can be easily removed.

FIG. 12 illustrates another example of a holding member 928, in which the length thereof is variable, so as to provide a user of the dressing with a desired elongation depending on the severity of the wound and/or other factors. The holding member 928 includes first and second portions 928A and 928B which are movable relative to each other. For example, the holding member 928 can include a sleeve 930 in which the first and second portions 928A and 928B can move in the direction of arrow A. The first and second portions 928A and 928B can have teeth on an end thereof which mate with a gear 934 which is rotatable on the sleeve 930. Rotation of the gear 934 results in the first and second portions 928A and 928B moving in the direction of arrow A. A knob 936 (shown in dashed lines) can be attached to the gear 930 to facilitate rotation of the gear 930. Thus, with holding member 928, the same dressing and holding member can be used to achieve different amounts of elongation for wounds of different severity.

FIG. 13 illustrates another dressing 940, in which one part of a hook and loop fastener 942 is attached to at least a portion of the adhesive portion 902 or portion 906 and the other part of the hook and loop fastener 944 is attached to at least a portion of a holding member 946. As discussed above, the holding member can be formed of a variety of materials such that it is rigid enough to maintain the portion 906 in the second shape (e.g., elongated) and may or may not be flexible to permit curvature of the dressing 940. When the dressing is desired to change to or towards its first shape (e.g., un-elongated), the hook and loop fastener bond is simply broken by removing the holding member 940.

FIG. 14 illustrates another dressing 950, in which each end portion 952A of a holding member 952 is adhered to a portion of the adhesive portion 902 or portion 906. Such adhesive bond can be removable or permanent. Where the bond is removable, the dressing is changed to or towards its first shape (e.g., un-elongated) by breaking the adhesive bond, i.e., by pulling the holding member 950 away from the portion to which it is adhered. Where the bond is permanent, the holding member can be cut or broken, such as at one or more weakened portions 954.

Referring now to FIGS. 15A, 15B and 15C, there is shown another embodiment of a dressing, referred to by reference numeral 960. The dressing 960 includes a clip 962 having a protrusion 964 with an opening 964. The clip 962 is retained in the portion 906b, such as with a loop 966 of material having an opening 968 for allowing the protrusion to extend from the portion 906b. The clip can be formed of plastic or metal or any material rigid enough for its intended purpose. A holding member 970 is used to maintain the portion 906b in a second shape, such as the portion 906b being elastic and the holding member 970 holding the portion 906b in an elongated state. The holding member 970 has ends 972, such as hooks, for engaging the opening 966 in the protrusion 964 of the clip 962. As discussed above, the dressing 960 is adhered to the skin about the wound by removing the release layers 904 and adhering the adhesive portions 902 to the skin. When the dressing 960 is desired to change to or towards its first shape (e.g., un-elongated), the holding member 970 is removed. Alternatively, the holding member 970 can be destroyed, such as by being cut or breaking the same about one or more weakened portions, as described above.

Figure 16C:
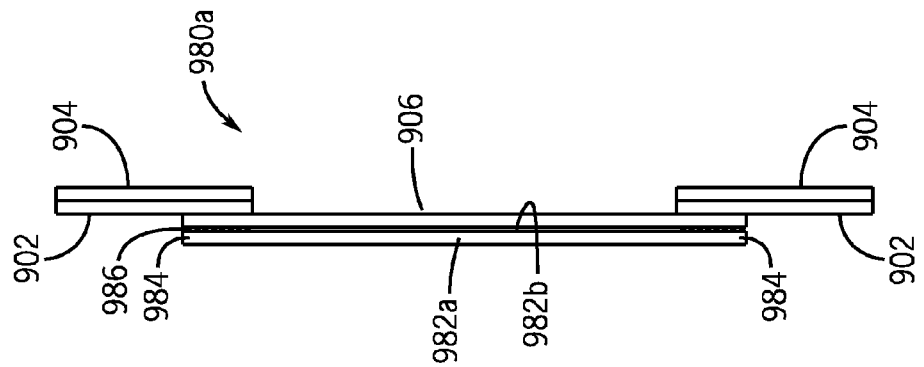
FIG. 16C illustrates a variation of the embodiment of FIGS. 16A and 16B.
Figure 16B:
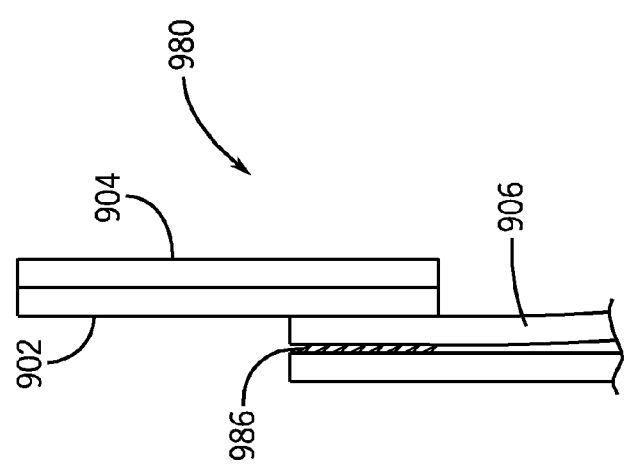
FIG. 16B illustrates a partial enlarged view of the dressing of FIG. 16A.
Figure 16A:
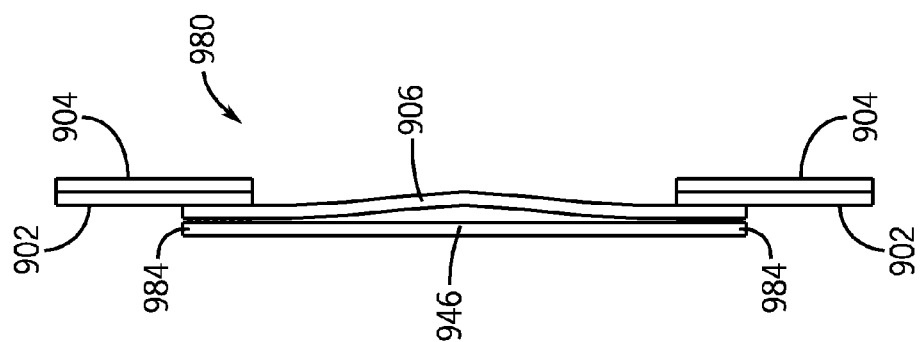
FIG. 16A illustrates yet another embodiment of a dressing.

Referring now to FIGS. 16A and 16B, there is shown yet another embodiment of a dressing, referred to generally by reference numeral 980. The dressing 980 includes a holding member 982 having a surface 984 at each end thereof made of individual barbs 984. The barbs 984 at each can be angled away from each other so as to grab the portion 906 (and/or adhesive portions 904) and maintain the portion 906 in a second shape, such as in an elongated state. The holding member 982 can be formed of a material with sufficient rigidity to maintain the portion 906 in the second (e.g., elongated) shape, such as metal or plastic. After the dressing 980 is adhered to the skin about the wound by removing the release layers 904 and adhering the adhesive portions 902 to the skin, the holding member 982 is removed such that the dressing 960 can change to or towards its first shape (e.g., un-elongated). Alternatively, the holding member 980 can be destroyed, such as by being cut or breaking the same about one or more weakened portions, as described above.

Referring now to FIG. 16C, there is shown a variation of the dressing embodiment of FIGS. 16A and 16B, referred to generally by reference numeral 980a and in which like features are denoted with like reference numerals. In the dressing 980a of FIG. 16C, the holding member 982a has the surface 984 at each end thereof made of individual barbs 984. The barbs 984 at each can be angled away from each other so as to grab the portion 906 (and/or adhesive portions 904) and maintain the portion 906 in a second shape, such as in an elongated state. In addition, an adhesive, connects at least part of the surface 982b between the portion 906 and holding member 982a to further maintain the portion 906 in the second shape.

Figure 17A:
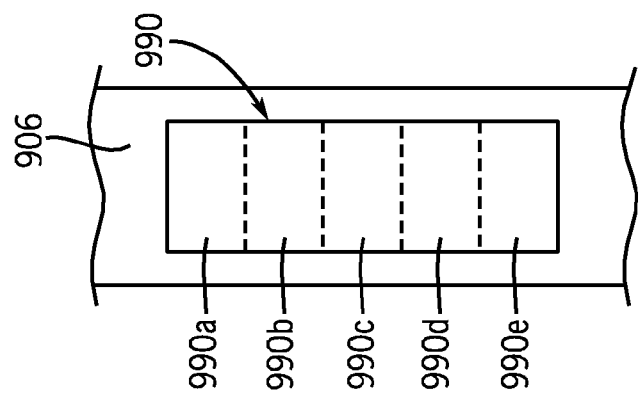
FIGS. 17A and 17B illustrate a variation of a dressing.
Figure 17B:
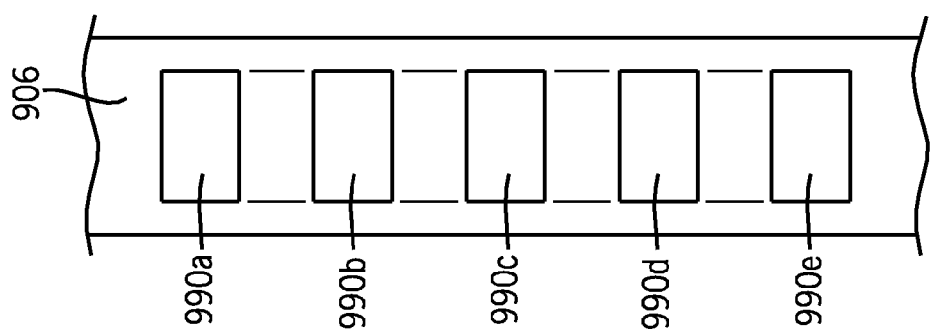

Referring now to FIGS. 17A and 17B, there is shown a variation for use with any of the embodiments described herein in which the portion 906 (906a, 906b) changes shape by being elongated. In such variation, the portion 906 includes a gauze pad 990 on a side thereof that contacts the wound. The gauze pad 990 includes strips 990a-990e. Although shown as 5 strips, the gauze pad 990 can be formed of two or more of such strips 990a-990e. The strips 990a-990e are positioned such that they form a continuous (or near continuous) gauze pad 990 when the portion is in its first un-elongated shape. That is, the strips 990a-990e accommodate the elongation of the portion 906 and separate when the portion 906 is elongated.

Figure 18A:
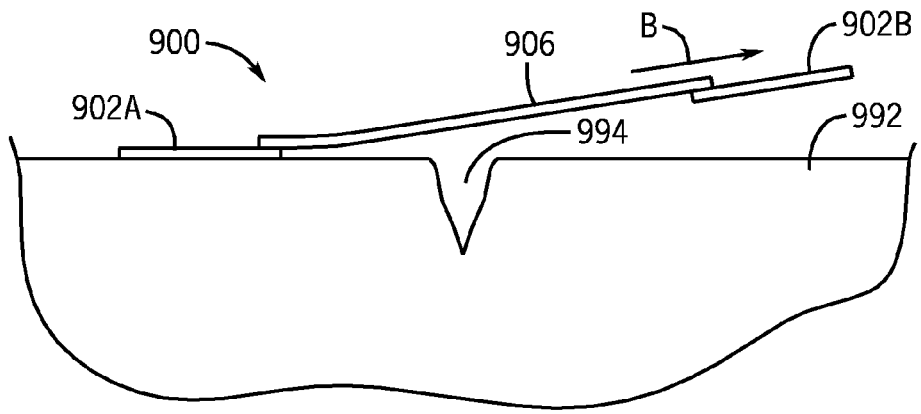
FIGS. 18A-18C illustrate a use of another alternative dressing.
Figure 18B:
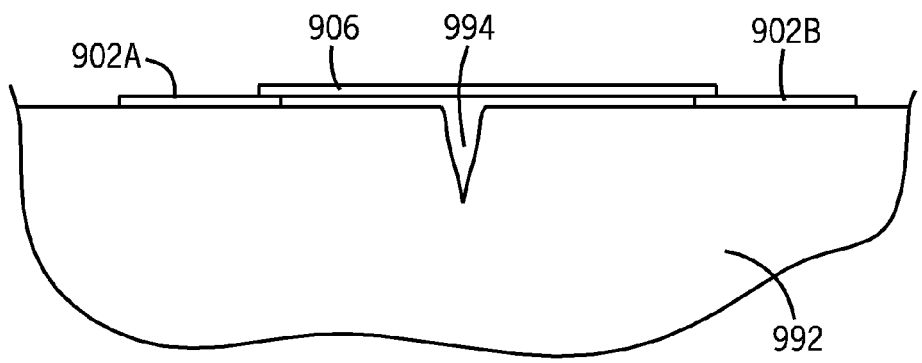
Figure 18C:
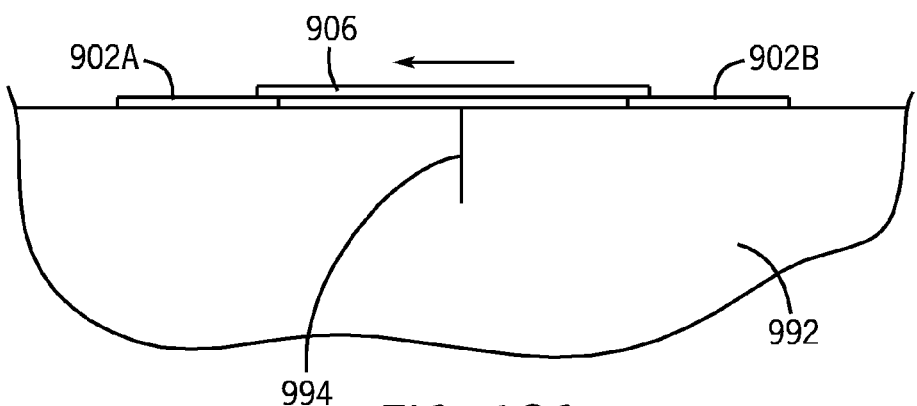

Referring now to FIGS. 18A-18C, the same illustrate an alternative use for the dressings illustrated above. Although applicable to the embodiments described above, the alternative use will be described by way of example with reference to the dressing of FIGS. 9, 9A and 9B. The alternative use for the dressing 900 does not make use of a holding member for maintaining the portion in a second (elongated) shape. As shown in FIG. 18A, one of the release members 904 is removed, exposing the adhesive on the adhesive portion 902A. The adhesive portion 902A is adhered to the skin 992 about a wound 994 to be closed/covered. With the release layer 904 from the other end removed, the dressing is urged into/towards its second shape, such as by pulling in the direction of arrow B and the other adhesive portion 902B is adhered to the skin 992 bridging the wound 994, as shown in FIG. 18B. The dressing 900 then tends to try to return to its first (un-elongated) shape resulting in the wound closing, as shown in FIG. 18C.

Thus, the alternative use described in FIGS. 18A-18C results in the wound closing with time, which, depending on the elastic force in the portion 906 and the severity of the wound, can be from a relatively short time to an extended time. The time delay results in less trauma to the patient because pulling the wound closed tightly at once can be painful. Furthermore, the portion can apply a constant pressure over time even though other variables change, such as a reduction in swelling. In dressings of the prior art, the dressing is pulled taught and applied to close the wound. However, such can be very painful to the patient and may not fully close the wound once swelling subsides.

The elastic force generated in the elastic portions described above can be due to a material that can be elastically deformed, such that it can be deformed into the second shape and be capable of elastically re-taking the first shape. An example of such a material is a woven material having at least one of a weft and warp fibers being elastic (e.g., formed of an elastomer, such as rubber) in the direction to be deformed (e.g., across the wound). Alternatively, at least one of the weft and warp fibers can be elastic in at least a component of the direction to be deformed.

Referring now to FIG. 19, the same illustrates an alternative portion 1000 for use in the embodiments discussed above in which the portion deforms from the second shape into the first shape. The portion 1000 is a woven fabric in which the weft and warp fibers 1002, 1004 are woven at an angle α offset from a stretching direction S, such as at 45°. Such a weaving pattern permits a central part B of the portion 1000 to have at least one of the weft and warp fibers 1002, 1004 to be elastic and other portions A to be at least partially formed such that the weft and/or warp fibers are non-elastic or less elastic than those used in part B. In this way, the central portion B of the portion 1000 can be elastic (e.g., elastically deform by stretching) and the other portions A be non-elastic (or less elastic). Thus, an adhesive for adhering the portion 1000 to the skin can be located on the other portions A and the stretchable portion B is disposed across the wound. This enables better adhesion of the portion 1000 to the skin and more effectively utilizes the elasticity of the portion 1000 and costs associated therewith by concentrating the elasticity only in the central portion that is associated with the wound. The adhesive for adhering portions of the portion 1000 to the skin, release members and holding member(s), if necessary, are not shown in FIG. 19 for the sake of simplicity.

Referring now to FIGS. 20a and 20b, the same illustrate a portion 1010 for use in the embodiments discussed above in which the portion deforms from the second shape (deformed, such as by being elongated) into the first shape (such as by being reduced in length and/or width). Such portion 1010 and others to follow can have integral or separate portions (e.g., 902) for adhering to the skin, as discussed above. If separate, such combination is still referred to hereinafter as a portion.

The portion 1010 can be formed of an elastic material that is at least capable of stretching in a direction S across a wound. The portion includes an elastic member 1012 formed thereon, such as by being adhered, embossed, attached by stitching, stapling, clipping or the like. The elastic member 1012 can be formed of materials capable of being elastically deformed, such as spring steel, plastic and the like. If stitched, the stitching 1014 can be at the points indicated by reference numeral 1014. The elastic member 1012 has a unrestrained shape 1012$b$, such as that shown in FIG. 20$b$, and is capable of being elastically deformed into a restrained (preloaded) shape 1012$a$, such as that shown in FIG. 20$a$. A restraining member, such as a tensile member, such as a string 1016, restrains the elastic member in the restrained shape 1012$a$. The restraining member 1016 can also be a rigid member. The restraining member can have a portion (not shown) to be grasped to facilitate pulling, cutting or breaking of the restraining member, such as a tab or knob. Thus, after adhering at least a part of the portion 1010 to the skin (or separately provided portions, such as portions 902 indicated above), as discussed above, with the elastic member 1012 corresponding to an area where a wound is located, the restraining member 1016 can be removed, such as by cutting or otherwise severing such that the elastic member 1012 can take the unrestrained shape 1012$b$ (or at least try to take such shape by moving from the restrained shape 1012$a$ towards the unrestrained shape 1012$b$) (the cut ends of the restraining member illustrated in FIG. 20$b$ by reference numerals 1016$a$). As the elastic member 1012 moves from the restrained shape 1012$a$ towards the unrestrained shape 1012$b$, the portion 1010 is reduced in length in the direction S. Rigid or semi-rigid bars 1018 (shown in broken lines) can be provided to facilitate the shape change along the width W (or portion thereof) of the portion 1010. The bars 1018 can be adhered or otherwise attached a surface of the portion 1010 or formed therein. Alternatively, the bars 1018 can be a more rigid portion of the portion 1010, such as by more densely formed weave or an embossing of the portion 1010.

FIGS. 20$c$ and 20$d$ illustrate a variation of the portion 1010 illustrated in FIGS. 20$a$ and 20$b$. The portion illustrated in FIGS. 20$c$ and 20$d$ being referred to by reference numeral 1010$a$ and having like reference numerals indicate like features. In the portion 1010$a$, the elastic member 1012 is arranged such that cutting or otherwise severing the restraining member 1016 while in the restrained shape 1012$c$ results in the elastic member 1012 taking the unrestrained shape 1012$d$ to elongate the portion 1010$a$ in the direction S.

Different shape, size, configuration and material elastic members 1012 can produce different desired changes in length (reduction or enlargement) depending on the desired effect.

FIGS. 20$e$ and 20$f$ illustrate another variation of the portion 1010 illustrated in FIGS. 20$a$ and 20$b$. The portion illustrated in FIGS. 20$e$ and 20$f$ being referred to by reference numeral 1010$b$ and having like reference numerals indicate like features. The portion 1010$b$ includes two restraining members, such as strings 1016 and 1016$b$. String 1016$b$ being longer or having additional elasticity than string 1016. Thus, the change in shape in the direction S can be accomplished in a stepwise manner by providing two (or more) restraining members. That is, cutting or otherwise severing restraining member 1016 permits the elastic member 1012 to take an intermediate shape 1012$e$ between the restrained shape 1012$a$ and unrestrained shape 1012$b$ because restraining member 1016$b$ is longer or more elastic than retraining member 1016. Once restraining member 1016$b$ is cut or otherwise severed, the elastic member can move towards the unstrained shape 1012$b$ shown in FIG. 20$b$. More than two restraining members can be provided to produce more than one intermediate shape of the elastic member.

FIGS. 21$a$-21$c$ illustrate another variation of the portion 1010 illustrated in FIGS. 20$a$ and 20$b$. The portion illustrated in FIGS. 21$a$ and 21$b$ being referred to by reference numeral 1010$c$ and having like reference numerals indicate like features. The portion 1010$c$ illustrated in FIGS. 21$a$ and 21$b$ is also configured to change shape in the direction S in a stepwise manner by providing two (or more) elastic members. The first elastic member 1012 is configured as shown and described in FIGS. 20$a$ and 20$b$ and additional elastic members, such as 1020, are also provided and configured similarly such that they are in a restrained shape 1020$a$ and move towards an unrestrained shape 1020$b$, shown in FIG. 21$c$. As shown in FIG. 21$b$, if the restraining member 1016 is cut or otherwise severed, the portion changes shape in the direction S, similarly to that shown and described with regard to FIG. 20$b$. Additionally, one or more of the restraining members 1022 can be cut or otherwise severed to produce an additional change in shape, as shown in FIG. 21$c$.

Alternatively, the plurality of elastic members (e.g., 1012, 1016) can be provided in the stretching direction S (similar to that shown in FIG. 25$a$ but configured for a reduction in the length of the portion) so as to stepwise and selectively reduce the length of the portion 1010$c$ in the stretching direction S. Such elastic members 1012, 1022 can be provided in the same sizes, different sizes, and configured for lengthwise and/or widthwise enlargement and/or reduction and/or components thereof.

FIGS. 22$a$-22$c$ illustrate a variation of the portion 1010$c$ illustrated in FIGS. 21$a$-21$c$. The portion illustrated in FIGS. 22$a$-22$c$ being referred to by reference numeral 1010$d$ and having like reference numerals indicate like features. The portion 1010$d$ illustrated in FIGS. 22$a$-22$c$ is configured to change shape in the direction S in a stepwise manner by providing two (or more) elastic members, similarly to that of portion 1010$c$. As in the portion 1010$c$, the first elastic member 1016 is configured as shown and described in FIGS. 20$a$ and 20$b$ and one or more additional elastic members, such as 1020 is also provided and configured similarly such that they are in a restrained shape 1020$a$ and move towards an unrestrained shape 1020$b$, shown in FIG. 21$c$. However, the additional elastic members 1020 are provided within the shape of the first elastic member 1016. As shown in FIG. 22$b$, if the restraining member 1016 is cut or otherwise severed, the portion 1010$d$ changes shape in the direction S, leaving the shape of additional elastic member 1020 unchanged (or changed but still capable of further change) similarly to that shown and described with regard to FIG. 20$b$. Additionally, the restraining member 1022 can be cut or otherwise severed to produce an additional change in shape, as shown in FIG. 22$c$. Although the bars 1018 are not shown in FIGS. 22$a$-22$c$, they can be provided for the benefits discussed above.

Figure 23:
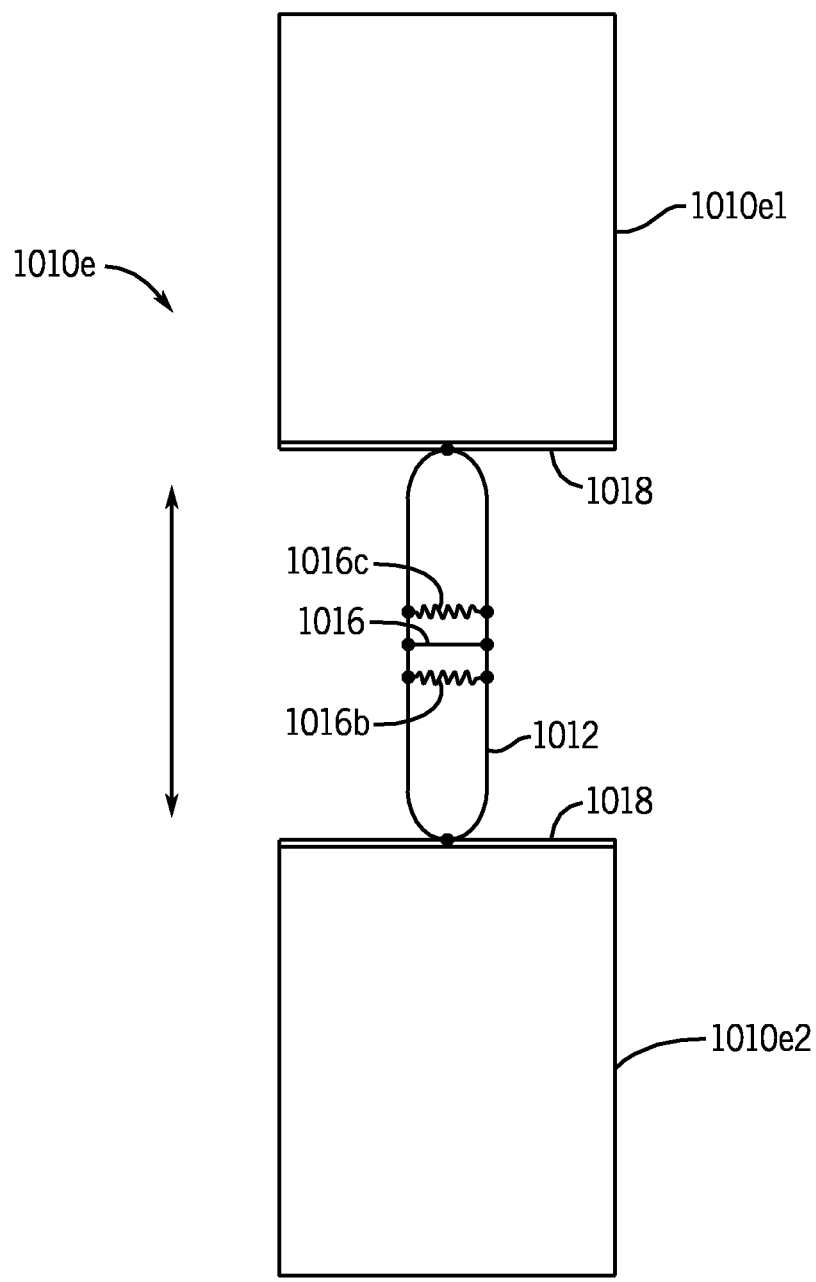
FIG. 23 illustrates an embodiment of a dressing portion.

Although the elastic members discussed above are shown attached to the portion and such portion changes shape (either stretches or shrinks along direction S) with the change in shape of the elastic member, such elastic member(s) as described above can be provided between first and second parts of the portion. Such a configuration is shown in FIG. 23. FIG. 23 illustrates a portion 1010e having first 1010e1 and second 1010e2 parts. Such parts 1010e1 and 1010e2 are connected by one or more elastic members 1012. Restraining members 1016, 1016b and 1016c having different lengths or degrees of elasticity can be provided to stepwise change the length of the portion in the direction S. The portion 1010e can be used without a dressing to cover the wound or a conventional dressing can be applied over the wound.

Although not shown, a single elastic member having a complex shape (more than one curved and/or linear segments) can be provided with more than one restraining member, such that cutting each restraining member incrementally changes the complex shape to incrementally change the shape of the portion across the wound, such as in the direction S. Thus, the stepwise change in shape in the direction S can be accomplished with a single elastic member and more than one restraining member arranged between various points on the complex shape.

Figure 24C:
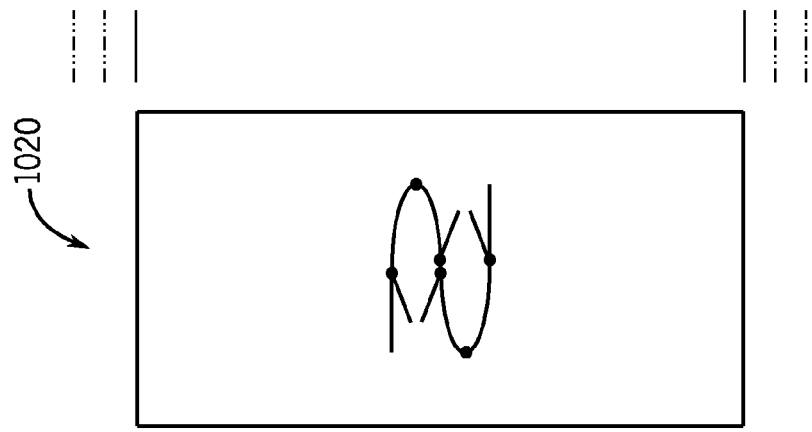
FIGS. 24a-24c illustrate another alternative dressing portion in which an elastic member having a complex shape is provided.
Figure 24B:
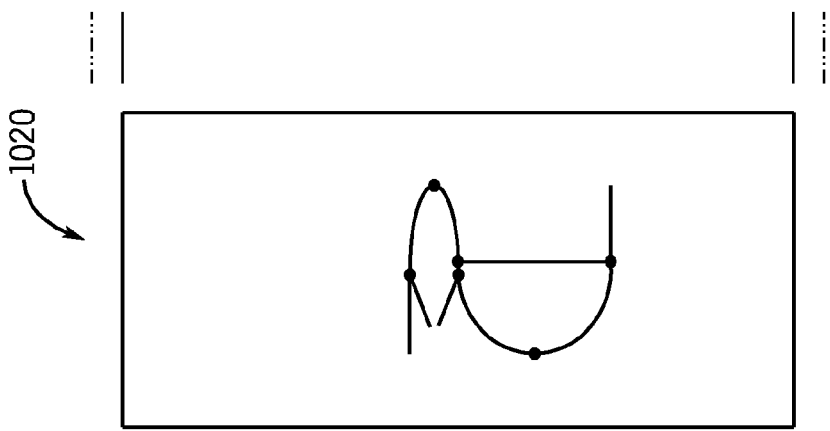
Figure 24A:
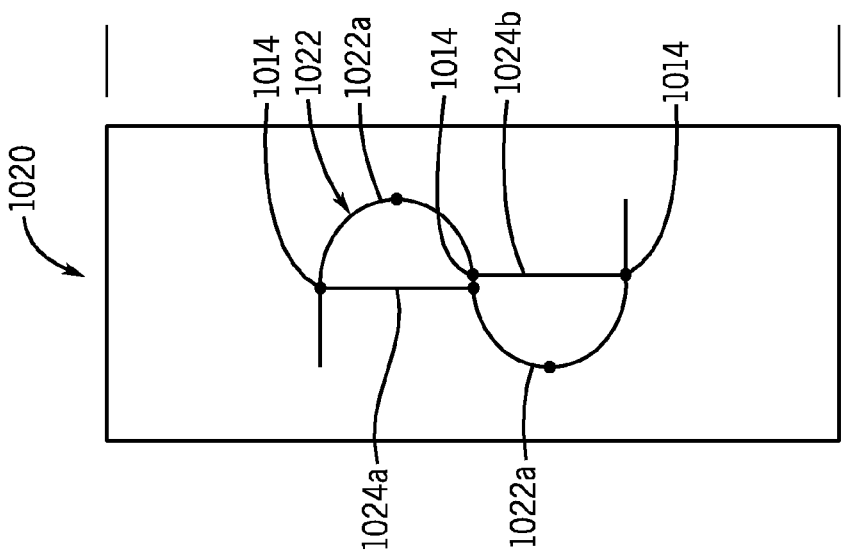

One such configuration is shown in FIGS. 24a-24c, generally referred to as dressing portion 1020. The portion 1020 includes an elastic member 1022 having a complex shape. Such shape can include multiple loops 1022a. Although two such loops 1022a are provided, one or more than two are also possible. Also, although the elastic member 1020 is shown attached to the dressing portion 1020 (which can be an elastic material, such as a fabric) at least at points 1014 (such as by stitching), the elastic member 1022 can be provided between parts of the dressing portion 1022, such as shown with regard to FIG. 23 and the bars 1018 discussed above can be utilized for the reasons set forth above. Also, although the elastic member 1022 is shown as an open shape, closed shapes can also be utilized. The loops 1022a are each fixed to the dressing portion 1022 to restrain the same in a first shape such that when the restraint is removed, each of the loops move towards a second shape which either tend to open or close a wound over which the dressing portion 1022 is applied (such as with an adhesive, as discussed above). Although the embodiment of FIGS. 24a-24c is described with regard to closing a wound, the elastic members can be configured to tend to open the wound. Furthermore, some of the loops 1022a can be configured for closing the wounds, while others configured to open the wound.

A restraining member 1024a, 1024b is provided between each loop 1022a, which when removed, such as by cutting or otherwise severing the same, removes the restraint on the loop 1022a and tends to close the loop (in the illustrated embodiment). In the configuration illustrated in FIGS. 24a-24c, the restraining members 1024a are rigid, As shown in FIG. 24b, when the restraining member 1024a is removed, such as by cutting, loop 1022a (at the top of the page) becomes smaller which reduces the length of the dressing portion 1020 to trend to close the wound. If additional closure is desired, restraining member 1024b can be removed from the lower loop 1022a, such as by cutting, to further reduce the length of the dressing portion 1020 as shown in FIG. 24c. Any number of such loops 1022a can be provided to selectively stepwise close or open the wound, as needed.

Figures 24D, 24E:
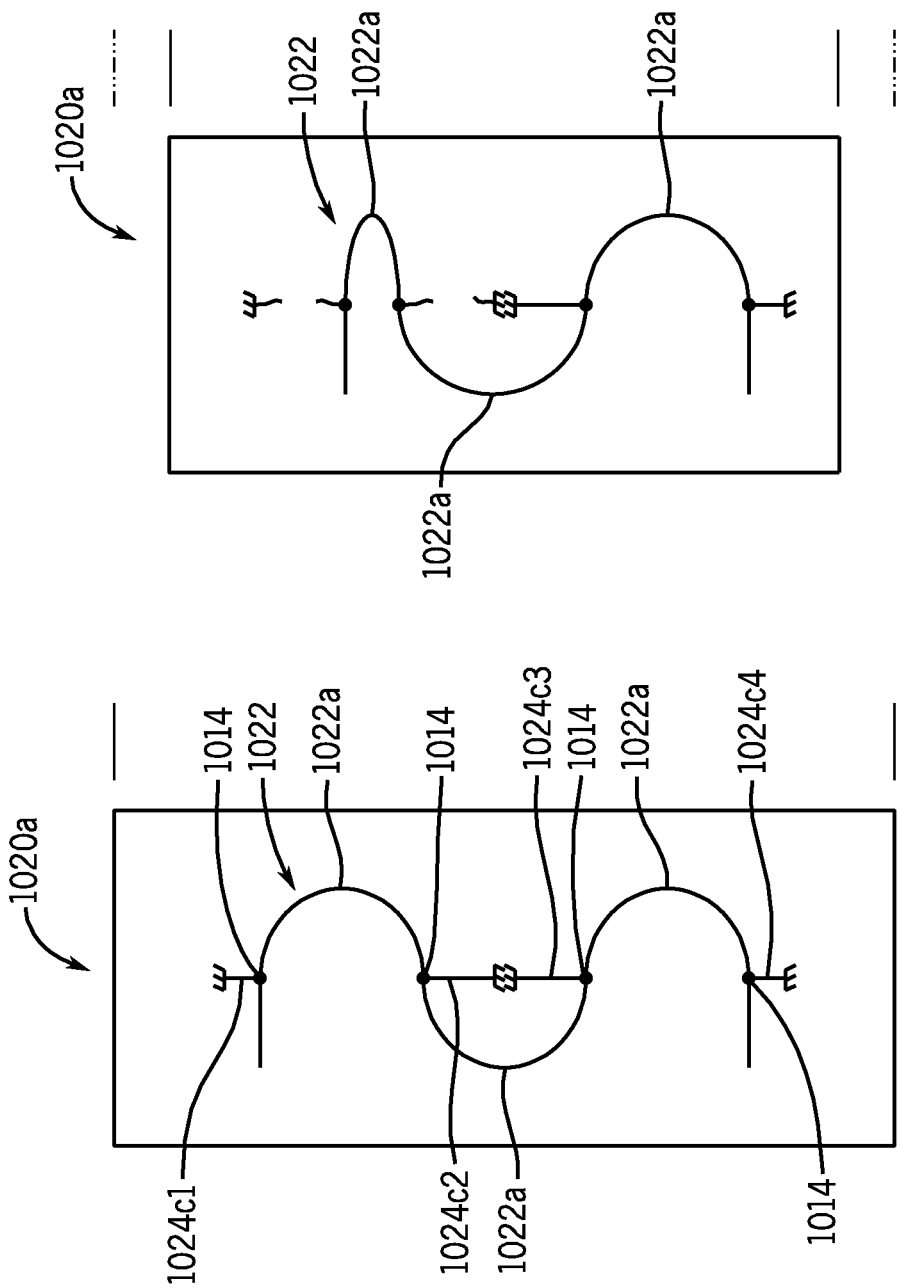

An alternative configuration of the dressing portion of FIGS. 24a-24c is shown in FIGS. 24d and 24e and generally referred to by reference numeral 1020a in which like reference numerals are used for like features. In the configuration of FIGS. 24d and 24e, a flexible restraining member is used, such as a string, which is fixed to the elastic member 1022 at one end and to the dressing portion 1020a at another end. The restraining member 1024 is cut or otherwise severed or removed to remove the restraint from the loops 1022a (there such loops 1022a are shown by way of example in FIGS. 24d and 24e). In the configuration of FIGS. 24d and 24e, a restraining member (1024c) is used for each leg of the loop 1022a. Thus, restraining members 1024c1 and 1024c2 are cut to remove the restraint from the top loop 1022a (and partially remove the restraint from the middle loop 1022a), as shown in FIG. 24e. Restraining members 1024c3 and 1024c4 can also be cut to remove the restraint from the bottom loop 1022a (and to remove the remaining restraint from the middle loop 1022a), Additional loops 1022a may be provided.

Figures 25A, 25B, 25C:
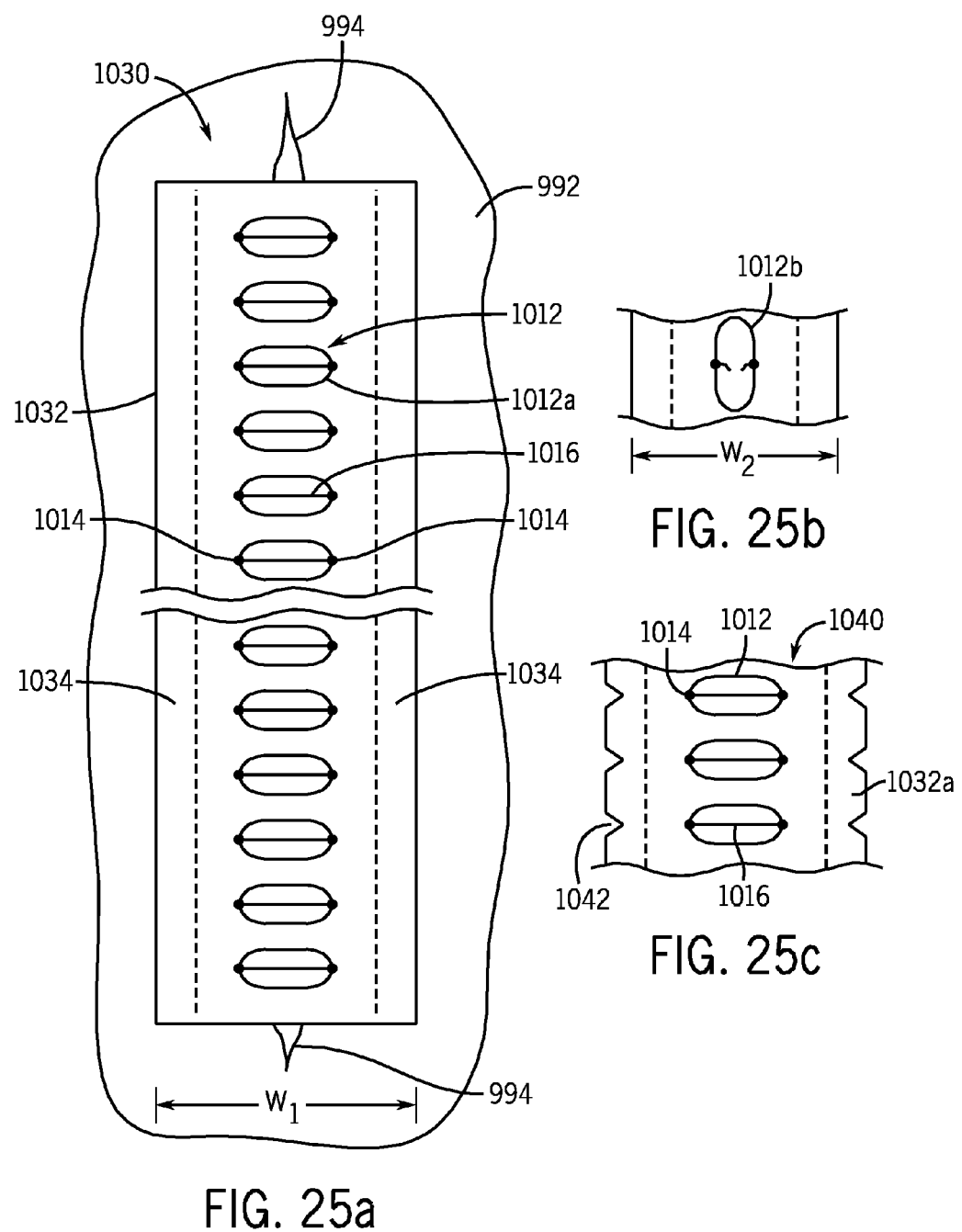
FIGS. 25a and 25b illustrate another alternative dressing portion in which multiple elastic members are provided along a length of the wound.
FIGS. 25c and 25d illustrate an alternative dressing portion of FIGS. 25a and 25b.

Referring now to FIGS. 25a and 25b, there is shown another embodiment of a dressing, generally referred to by reference numeral 1030. The dressing includes a portion 1032 for covering the wound, which is flexible, such as an elastic material or fabric. On a side of the portion 1032 that faces the skin 992, an adhesive 1034 is applied, such as along a peripheral edge of the portion 1032. Release layers (not shown) are also provided, as discussed above, over the adhesive 1034 and removed when the portion 1032 is to be adhered to the skin 992. The portion 1032 includes a plurality of elastic members, such as elastic member 1012 configured as shown and described in FIGS. 20a and 20b along a length of the dressing 1030. The elastic members 1012 are configured such that removing a restraint thereon tends to close a wound 994 over which it is applied in the width direction. Thus, as shown in FIG. 25b, when the restraint is removed, such as by cutting the restraining member(s) 1016, a corresponding part of the portion 1032 changes shape from a first width W1 to a smaller width W2. Dressing 1032 is particularly useful for longer wounds. As shown in FIG. 20e, each of the elastic members 1012 may be provided with more than one restraining member such that the amount of closure (change in width) can be varied over the length L of the dressing 1032, which may be particularly useful for wounds that may be irregular in that the amount of closure necessary may vary over the length of the wound. Such dressing may be configured in any of the ways discussed above, such as opening a wound.

Figure 25D:
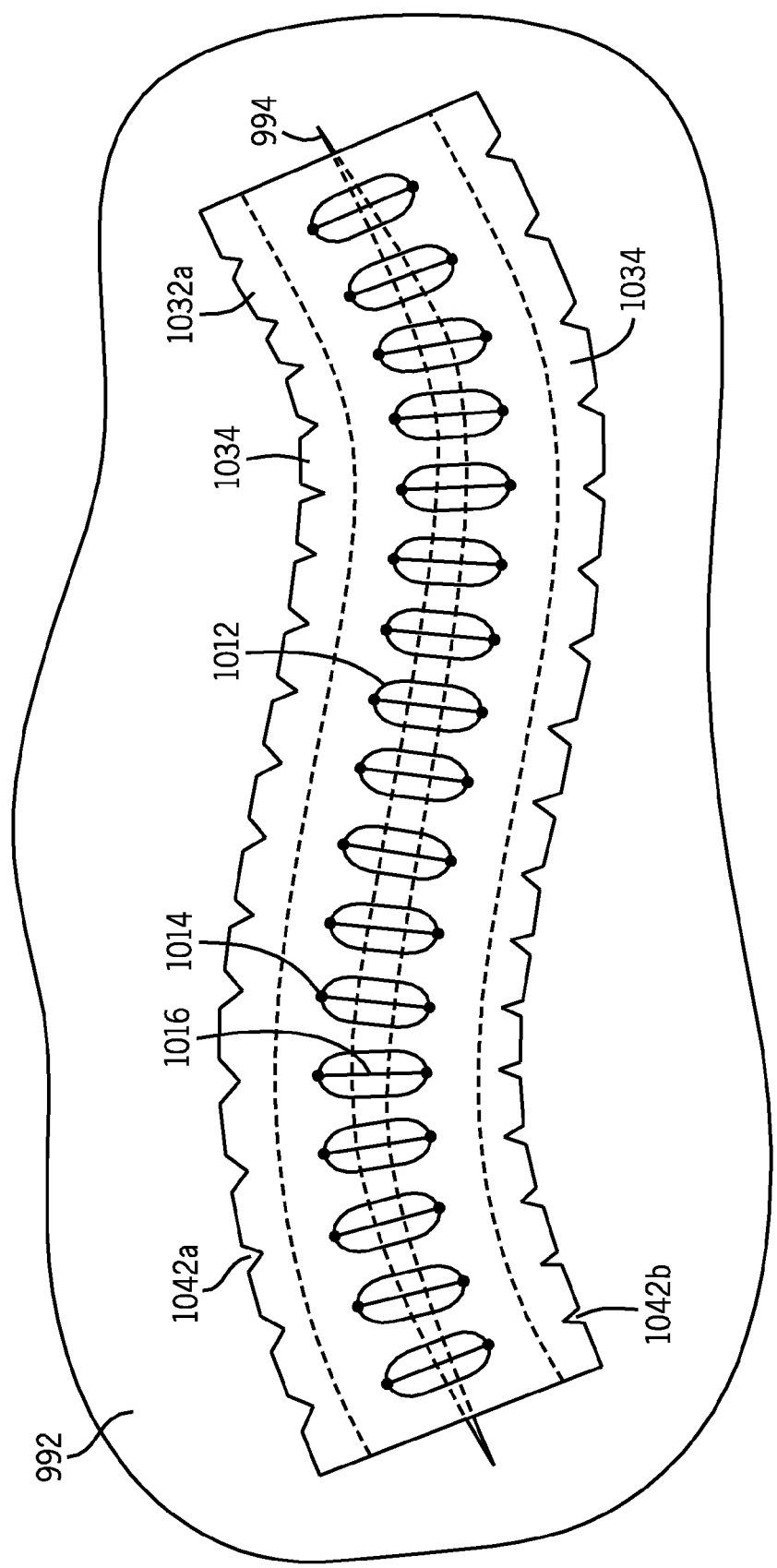

Referring now to FIGS. 25c and 25d, there is shown a variation of the dressing 1030 shown in FIGS. 25a and 25b, such dressing being generally referred to by reference numeral 1040 and in which like reference numerals refer to like features. As shown in FIG. 25c, the dressing 1040 includes an edge that facilitates curving the portion 1032a, such as a series of notches 1042. Other means of facilitating curvature of the portion 1032a, such as a series of slits or additional elasticity of the portion 1032a at the edges may also be used. as shown in FIG. 25d, the portion 1032a can be easily curved and applied over an irregularly shaped (non-linear) wound 994 by opening some of the notches 1042a and closing others 1042b.

The dressings 1030 and 1040 can be provided in large lengths, such as on a roll, and cut to the desired length. Although many of the dressings shown above are shown with a portion of the wound 994 extending past a periphery of the dressing, such is shown so as to illustrate a closure of the wound. Those skilled in the art will appreciate that the dressing can completely cover the extent of the wound.

Furthermore, although the dressing described above are discussed with regard to closing or opening a wound, such a use is not necessary. For example, the dressing may have utility for other uses for applying an elongating or reducing pressure on the skin. For example, the dressing can apply an elongating pressure, particularly incrementally over time, to stretch the skin in advance of a surgical procedure in which extra skin is necessary, such as to provide extra skin that is excised for other portions of the body, such as burned portions. In such an exemplary procedure, the dressing will be less traumatic than conventional skin stretching procedures which require an implant of an expanding device. Although used for purposes other than dressing a wound, the dressing will still be referred as such (i.e., as a dressing although capable of other uses).

Referring now to FIGS. 26a-26f, there are shown two additional embodiments of a dressing, generally referred to by reference numerals 1050 and 1100, respectively. A first of such embodiments is shown in FIGS. 26b and 26e, a second of such embodiments being shown in FIGS. 26c and 26f, with FIGS. 26a and 26d being common to each of the two embodiments.

Referring first to FIG. 26a, the dressing 1050, 110 includes an adhesive ring portion 1052 formed of a material, such as plastic film or woven fabric and having an adhesive 1054 on a surface corresponding to a surface contacting the skin 1056 around a wound, such as a puncture wound 1058. A first elastic member 1060a, 1060b is formed in a first shape, such as having a convex (slightly cured away from the skin/adhesive) shape 1060a or concave (slightly curved towards the skin/skin adhesive) shape 1060b and attached to the adhesive ring 1054, by any means known in the art, such as by stitching, adhering, heat welding etc. The first elastic member is capable of being deformed into a second shape, such as those shown in FIGS. 26b and 26c by a second elastic member 1062. The second elastic member is fixed to the dressing, such as around an inner periphery of the adhesive ring 1054 at a free end 1062a, such as by adhering, stitching, stapling, clipping, heat welding or the like. The second elastic member 1062 is restrained into a shape, such as shown in FIG. 26a by a restraining member 1064, which can be a rigid member fixed to the second elastic member at at least two points, such as by adhering or the like. Such restraining member 1064 can also be integrally formed with the second elastic member 1062. Thus, the restraining member 1064 restrains the second elastic member 1062 into a shape that further restrains the first elastic member 1060a, 1060b into the first shape, as shown in FIGS. 26b and 26c. Alternatively, restraining members can be used to restrain each of the first elastic member 1060a, 1060b and second elastic member 1062 and additional restraint can be used to restrain the first elastic member 1060a, 1060b in its restrained shape (such as by releasably fixing a lower surface of the restraining member 1064 to an upper surface of the first elastic member 1060a, 1060b.

When the restraint is removed, such as by cutting or otherwise severing the restraining member 1064, the restraining member 1064 coils up on itself such that its diameter is reduced, thereby removing restraint from the first elastic member 1060a, 1060b to both reduce the diameter of the dressing from D1 to D2 and to cup the first elastic member 1060a, 1060b either upwards from the skin 1056, as shown in FIG. 26e, or downwards into the skin 1056, as shown in FIG. 26f. Thus, the reduction in diameter applies a pressure to the wound to close the same, as shown in FIGS. 26e and 26f and the cupping of the first elastic member 1060a, 1060b additionally either provides a sealed evacuated environment for the wound (which could be cut, puncture or a blister 1058a caused by a thermal or chemical burn), as shown in FIG. 26e, or apply pressure to the wound to stop bleeding, as shown in FIG. 26f. Where the first elastic member 1060a cups upward, the second elastic member 1062 can be configured with a larger diameter such that its unrestrained shape (see FIG. 26d) does not interfere with the upward movement of the first elastic member 1060a. After the dressing 1050, 1100 is applied to the skin and the restraining member 1064 is removed, such as by cutting, it can be fully removed from the dressing, such as by cutting it off at its ends or breaking the same at its ends, such as by providing a weakened portion at the ends that facilitate breaking. Also, the second elastic member 1062 can also be fully removed from the dressing after its restraint is removed and the first elastic member takes its desired shape, such as by removing the fixation of the first elastic member.

The dressings 1050, 1100 can be configured with any of the features and for any uses discussed in co-pending U.S. application Ser. No. 13/008,881 filed on Jan. 18, 2011, the entire contents of which is incorporated herein by reference.

Referring now to FIGS. 27a-27c, there is shown an embodiment of a dressing which adds one or more elastic members to the dressing of FIGS. 18a-18c, such as that illustrated in FIGS. 20a and 20b. Like reference numerals in FIGS. 27a-27c indicate like features to those shown in FIGS. 18a-18c, 20a and 20b. The dressing 992a is applied as described with regard to FIGS. 18a-18c. However, one or more elastic members, such as the one described with regard to FIGS. 20a and 20 and indicated by reference numeral 1012 is provided. Therefore, as shown in FIG. 24b, if the dressing does not fully close the wound 994, or if the wound 994 needs extra closing after time (e.g., during the healing process such as after swelling subsides), the elastic members 1012 can be closed to provide any additional closure to the wound, as shown in FIG. 27c. Similarly, the elastic member can be configured to opening the wound or otherwise providing an enlarging pressure to the skin.

The portions disclosed above may be elastic, inelastic or partly elastic, and can be configured to conform to the changes in the configuration of aforementioned elastic members.

Any of the portions shown in FIGS. 20e-27 can be configured to change shape by elongating or enlargement (as shown in FIGS. 20c and 20d) instead of by reducing in length in the direction S.

Although the restraining members 1016, 1016b, 1016c are described above as being cut or severed, they can be released from restraining the elastic members in different ways, such as being glued or otherwise attached to the elastic member at various points 1014 and such attachment being disconnected, such as by pulling the restraining member(s) or a portion attached thereto to break the attachment.

The elastic members in any of the embodiments discussed above can also be cut or otherwise severed after they take their unrestrained shape if it is desired that the application of force resulting from the elastic member(s) is no longer desired. Such cutting can be along a cross-sectional area thereof or such elastic members can be broken along a cross-section portion, such as at a weakened portion. The weakened portion can be of any type known in the art, such as by providing a perforated portion or a reduced cross-sectional area portion to facilitate the breaking.

The elastic members discussed above, may be provided in any material, shape, configuration and attachment to the dressing portion such that it deforms from a first shape to a second shape for a desired effect. Some examples of materials are plastics capable of elastic deformation and metals capable of elastic deformation, such as spring steels.

Examples of shapes of the elastic members are discussed above but is not exhaustive of the possible shapes, sizes and configurations of the elastic members that can be utilized for any given desired effect. The elastic members can be fixed to a surface of the dressing portion, such as by stitching or adhering, at at least enough points to provide the desired effect brought about by the shape change when the preloading of the elastic member is released by releasing a restraint which maintains the elastic member in the preloaded shape. The elastic member can also be formed at least partially integrally with the dressing portion, such as being embossed into the dressing portion or embossed with an interior insert of a material capable of elastic deformation. The elastic members can also be formed inside the dressing portions, such as by being woven in an interior of the dressing portion.

Figure 28:
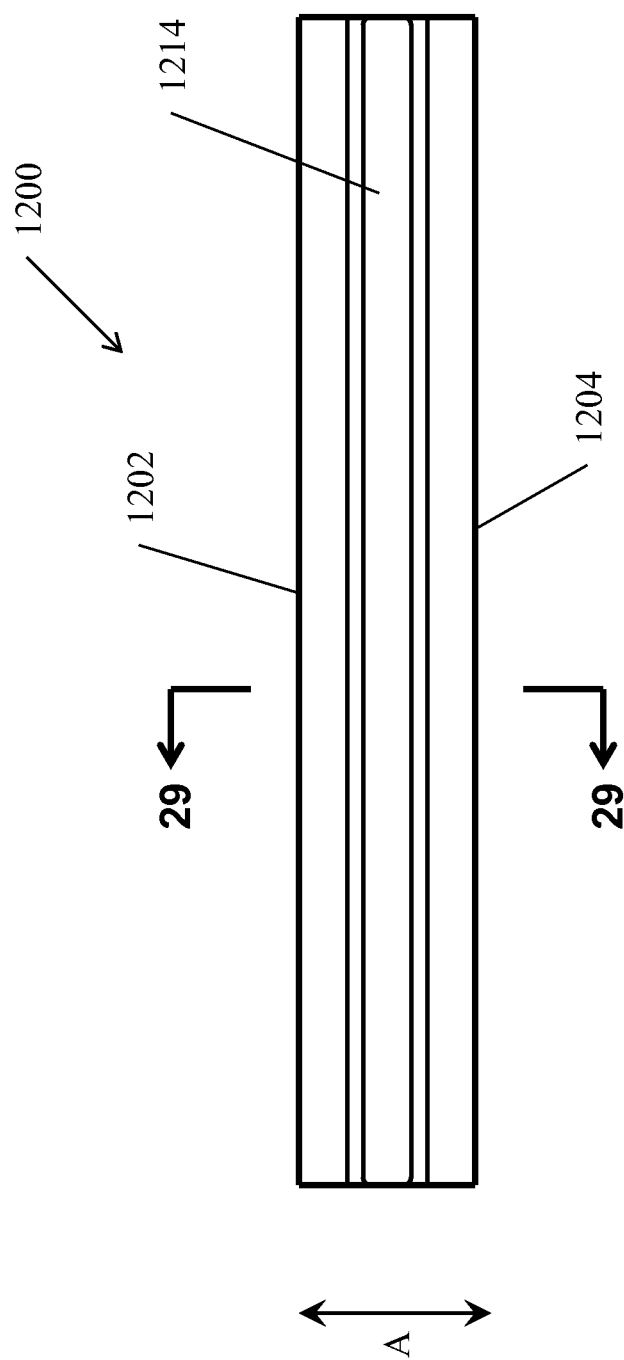
FIG. 28 illustrates a top view of an additional embodiment of a dressing for closing wounds.
Figure 29:
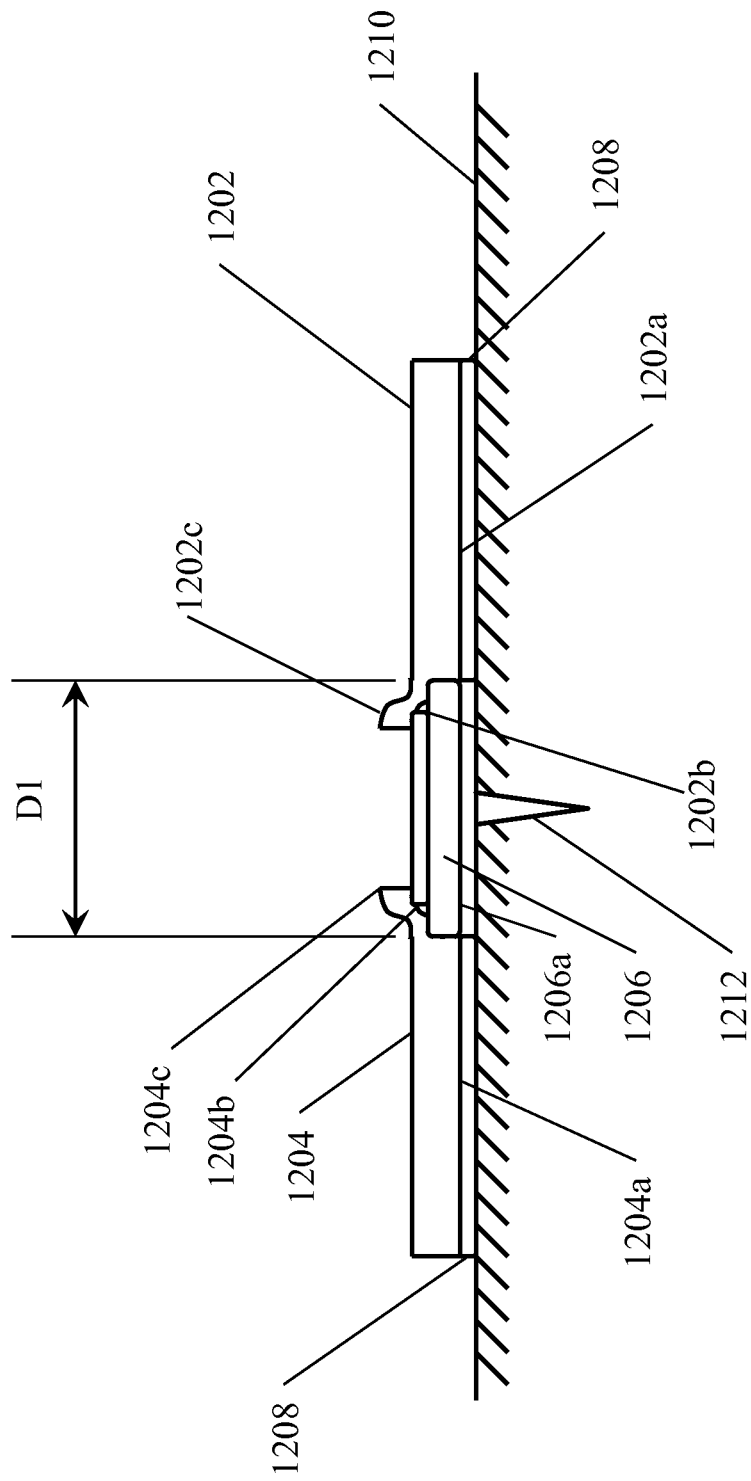
FIG. 29 illustrates a sectional view of the dressing of FIG. 28 as taken along line 29-29 where the locking member has not been removed and the wound is open.

Referring now to FIGS. 28 and 29, there is shown another embodiment of a dressing, generally referred to by reference numeral 1200. The dressing 1200 includes first and second bandage portions 1202, 1204 connected by an elastic material 1206 being elastic in at least a direction A towards the first and second bandage portions 1202, 1204 such that stretching the elastic material 1206 to pull the first and second bandage portions 1202, 1204 apart results in a biasing force tending to pull the first and second bandage portions 1202, 1204 together. The first and second bandage portions can be formed of a fabric or of a relatively rigid or semi-rigid material, such as a thin plastic sheet-like material. The elastic material 1206 can be formed of any material having elastic properties, such as an elastomer or a fabric having elastomer fibers woven in at least the direction A. An underside 1202a, 1204a of the first and second bandage portions 1202, 1204 corresponding to a surface of the skin to which the same are to be applied, include an adhesive 1208 for adhering the first and second bandage portions 1202, 1204 to the skin 1210. In use, the dressing 1200 is disposed on the skin 1210 such that a wound 1212 corresponds with the material 1206. An underside 1206a of the elastic material may include a gauze material (not shown) for contact with the wound 1212.

A locking member 1214 is disposed between the first and second bandage portions 1202, 1204 to maintain the elastic material 1206 in a stretched state (D1), as shown in FIG. 29. The locking member 1214 can be relatively rigid such that it maintains the elastic material 1206 in the stretched state (D1) without buckling (although some buckling may be permitted). The first and second bandage portions 1202, 1204 may have an abutment surface 1202b, 1204b to facilitate keeping the locking member 1214 urging against the first and second bandage portions 1202, 1204. Furthermore, in addition to or in place of the abutment surfaces 1202b, 1204b, or the first and second bandage portions 1202, 1204 may include a projection 1202c, 1204c for creating a partially enclosed space above the elastic material 1206 so as to dispose the locking member 1214 therein and prevent the same from being unintentionally moved from between the first and second bandage portions 1202, 1204. The projections 1202c, 1204c and/or the locking member 1214 can be able to be physically deformed to allow the locking member 1214 to be removed from between the first and second bandage portions 1202, 1204. The projections 1202c, 1204c can be formed integrally with the first and second bandage portions 1202, 1204 or fixed thereto.

In use, a release layer (not shown in FIG. 29, but assumed to be similar to that shown in FIG. 9A, reference numeral 904) is releasably adhered to the adhesive on the underside of the first and second bandage portions 1202, 1204 such that it can be removed when the adhesive is to be adhered to the skin. As discussed above, the dressing 1200 is disposed on the skin 1210 such that a wound 1212 corresponds with the elastic material 1206. That is, the first and second bandage portions 1202, 1204 are adhered to the skin 1210 about the wound 1212 such the wound corresponds to the elastic material and the biasing direction of the elastic material 1206 would tend to close the wound 1212.

Figure 30:
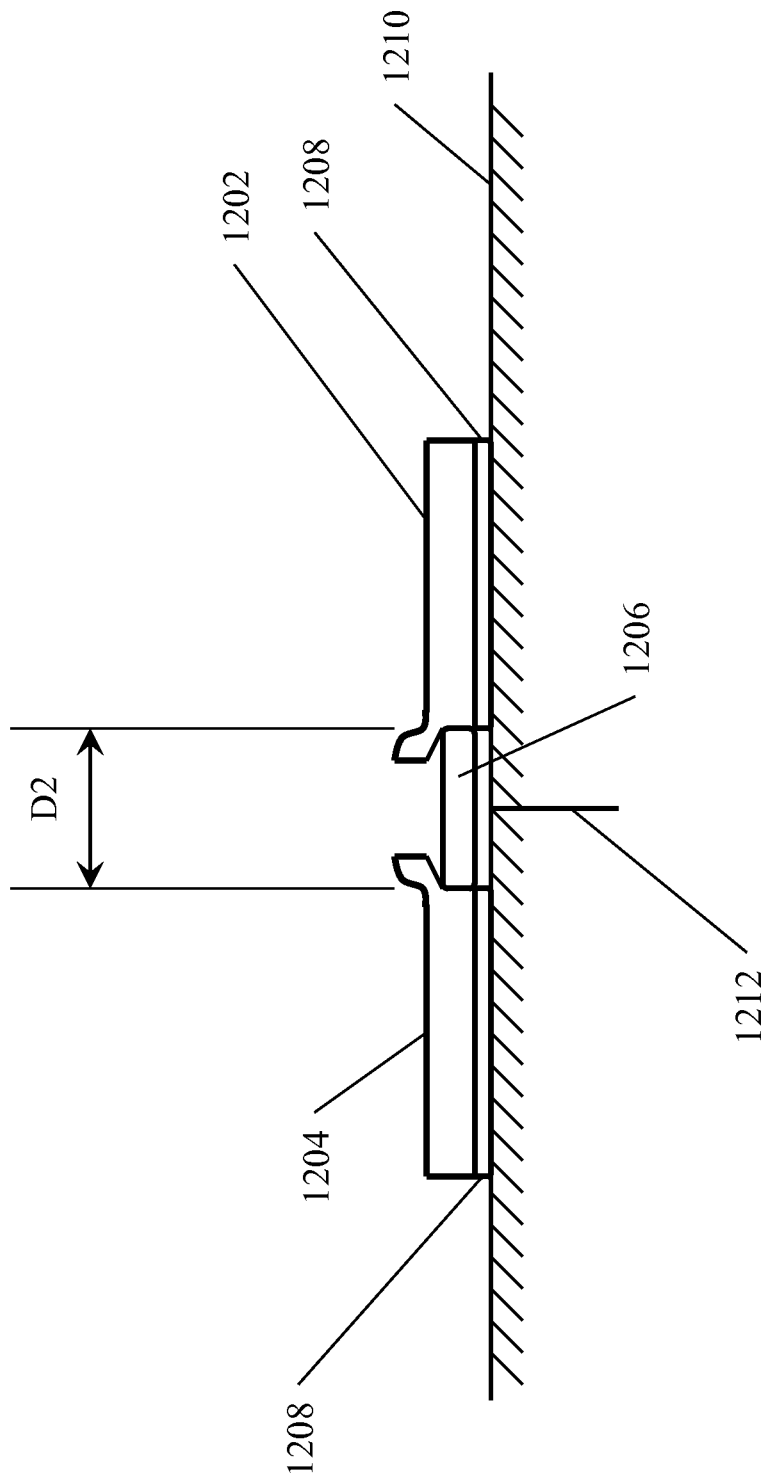
FIG. 30 illustrates the section view of FIG. 29 where the locking member has been removed and the wound is closed.

Referring now to FIG. 30, the locking member 1214 is removed by pulling it from between the first and second bandage portions 1202, 1204 causing the elastic material 1216 to pull the first and second bandage portions 1202, 1204 towards each other. The locking member 1214 may have a portion formed therein or attached thereto, such as a string or tab for facilitating the pulling of the same from the first and second bandage portions 1202, 1204. Since the first and second bandage portions 1202, 1204 are adhered to the skin 1210, the skin adhered to each of the first and second bandage portions 1202, 1204 is also pulled together, resulting in the wound 1212 closing (as shown in FIG. 30). The elastic material 1206 shrinks to a state D2 having a dimension across the wound 1212 smaller than the dimension in the state D1 shown in FIG. 29.

Figure 31:
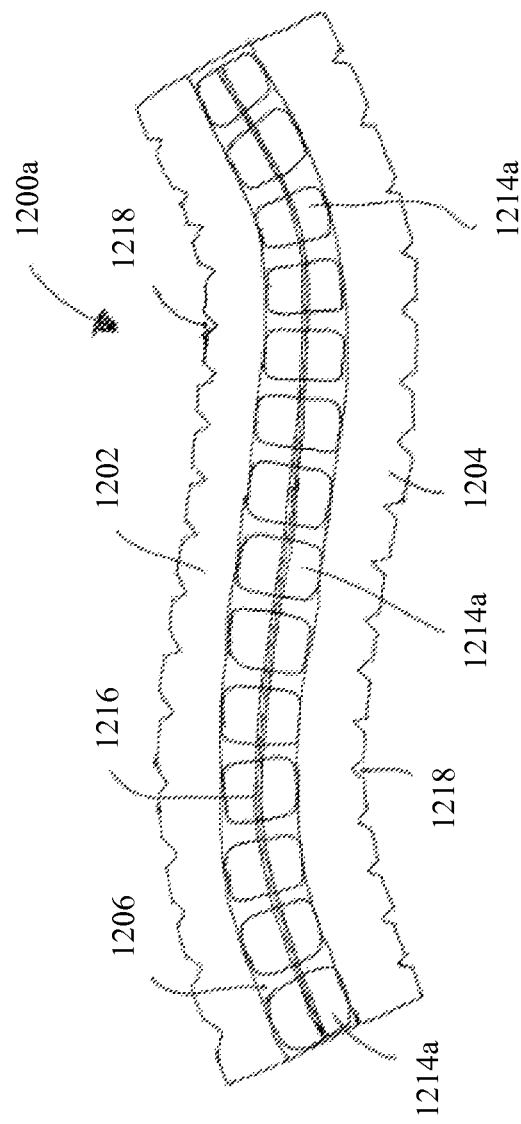
FIG. 31 illustrates a variation of the dressing of FIG. 28 in which the dressing is configured to facilitate curving the same about an irregular shaped wound.

Similarly to the dressing illustrated in FIG. 25d, the dressing of FIGS. 28-30 can include notches 1218 formed on a periphery of the first and second bandage portions 1202, 1204 to facilitate curving the dressing 1200a about an irregularly shaped wound. Such dressing 1200a is illustrated in FIG. 31 (with the projections 1202c, 1204c not shown for clarity). In such a configuration, the locking member 1214 may be similarly notched or intermittently formed so as not to be a continuous member but formed of a series of locking members 1214a, which can be connected by a flexible member 1216, such as a string, fabric or the like. Forming the locking member 1206 non-continuous as a series of locking members 1214a also facilitates forming the dressing 1200a in a large roll and cutting the same to a desired length (between any two of the series of locking members 1214a).

Figure 32:
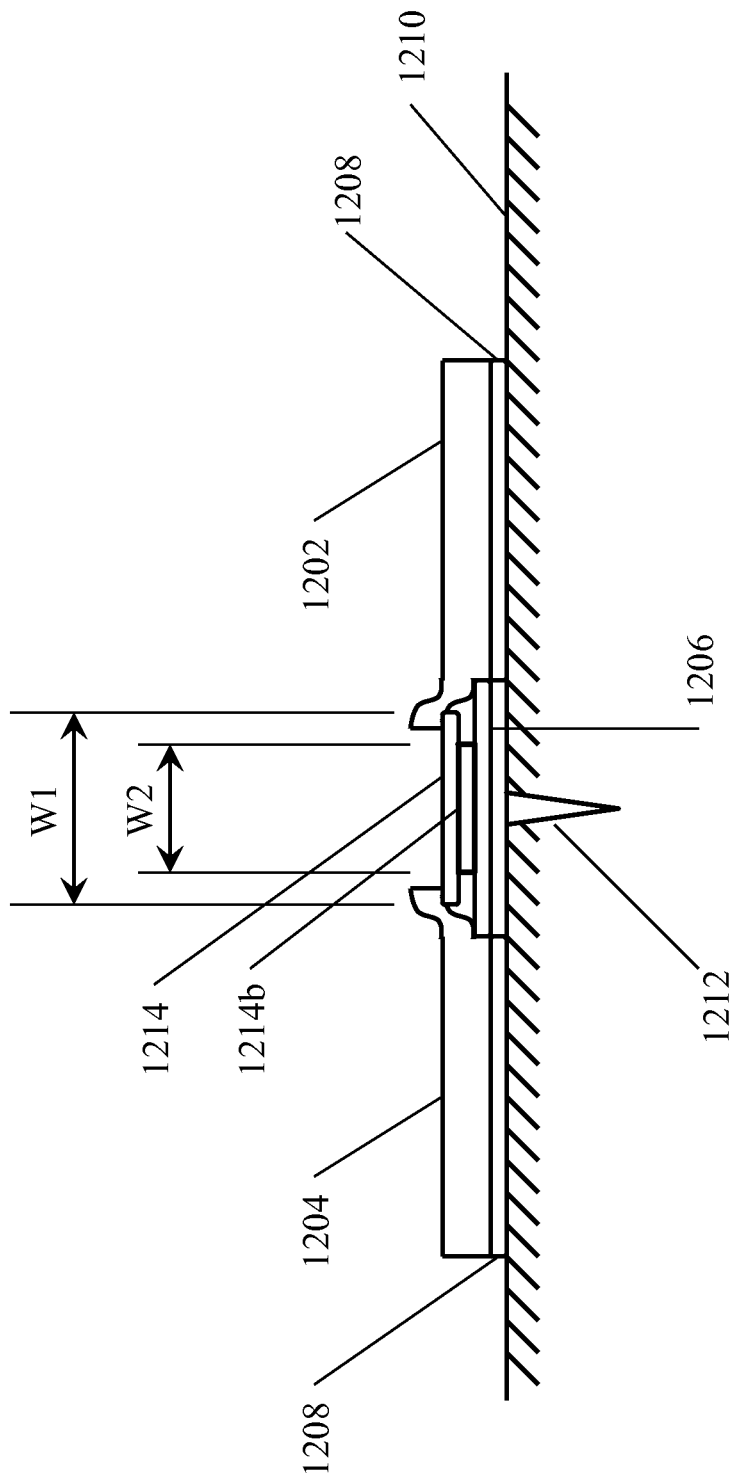
FIG. 32 illustrates a sectional view (as if taken along line 29-29 in FIG. 28) of another variation of the dressing of FIG. 28.

Referring now to FIG. 32, there is shown another variation of the dressing of FIG. 28, in which like features are designated by like reference numerals. In the dressing of FIG. 32, more than one locking member is disposed between the first and second bandage portions 102, 104. The dressing of FIG. 32 includes a first locking member 1214 having a first width W1 and a second locking member 1214b having a second width W2. The second width W2 being smaller than the first width W1 such that after the first locking member 1214 is removed, the elastic material 1206 is restrained to only partially shrink, until the first and second bandage portions 1202, 1204 abut the second locking member 1214b. Subsequently, the second locking member 1214b can be removed to allow the elastic material 1206 to continue shrinking in the direction across the wound 1212. Thus, the closure of the wound 1212 can be applied in stages (e.g., the removal of the first locking member 1214 can close the wound 1212 fully, however, after swelling subsides and the wound 1212 partially re-opens, the second locking member 1214b can be removed to fully close the wound 1212 once again). Although shown with first and second locking members 1214, 1214b, more than two locking members can be provided. Those skilled in the art will appreciate that the closure of the wound in stages can be accomplished without multiple locking members, for example, by allowing the locking member 1214 in FIG. 29 to be partially removed, such as by collapsing in the direction across the wound before being entirely removed.

Figure 33:
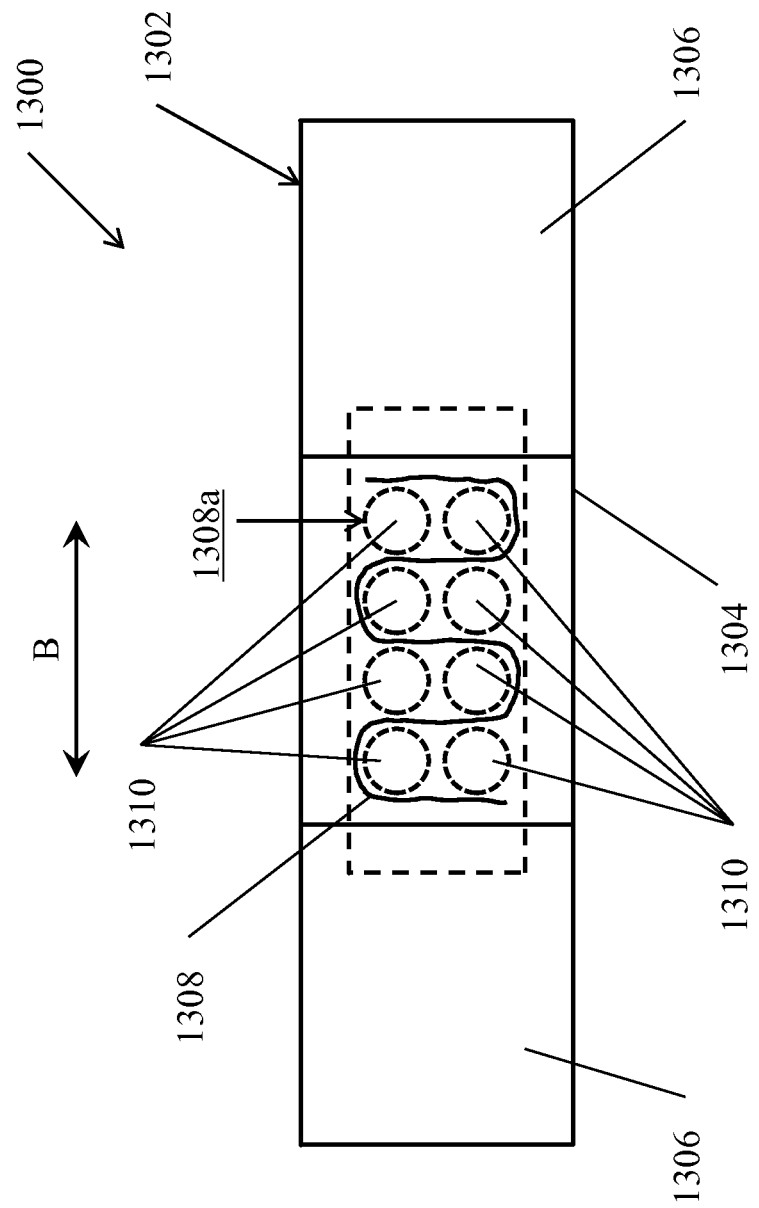
FIG. 33 illustrates a top view of another embodiment of a dressing for closing wounds (shown with the locking member in broken lines for clarity).

Referring now to FIG. 33, there is shown another embodiment of a dressing, generally referred to by reference numeral 1300. The dressing 1300 includes a dressing material 1302 applied to a wound, blister, burn etc. The dressing includes a central portion 1304 having a gauze and being elastic in at least direction B. The dressing material 1302 further includes first and second adhesive portions 1306 having an adhesive applied to one surface thereof for application to the skin (as discussed above). An elastic element 1308 being biased in an open position is associated with the central portion 1304, such as being fixed thereto by stitching, adhering or in any manner as discussed above. The elastic element 1308 is biased open by retraining members 1310 such that removal of the restraining members would tend to close the elastic element such that the central portion 1304 would shrink in the direction B to close a wound corresponding to the central portion 1304. The restraining members 1310 can be attached to a common backing 1312 (shown in broken line in FIG. 33 so as not to obscure the restraining members 1310).

Figure 34:
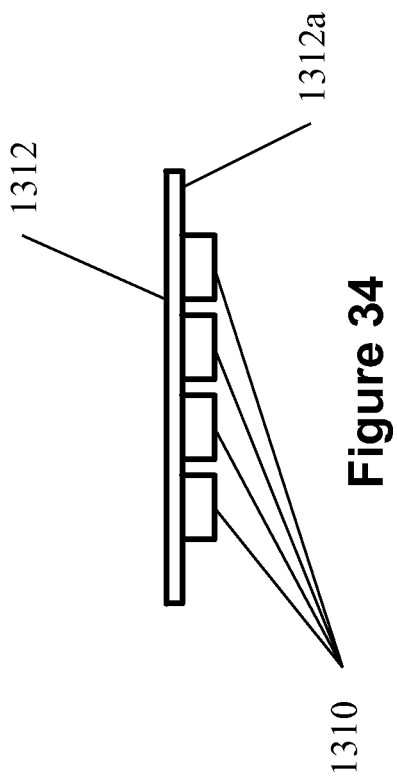
FIG. 34 illustrates a side view of a first variation of locking member for use with the dressing of FIG. 33.

Referring now to FIG. 34, the restraining members 1310 and backing 1312, which can be formed individually and assembled or formed integrally, such as by molding, is illustrated therein. The restraining members are disposed within the folds 1308a of the elastic member 1308 such that they bias the elastic member 1308 open and prevent the elastic member from closing. After application of the dressing 1300 to the skin with the wound corresponding to the central portion 1304, the backing 1312 can be removed by pulling an end 1312a thereof which results in the restraining members 1308 also being removed from the folds 1308a of the elastic member 1308, which in turn causes the elastic member 1308 to close the wound.

Figure 35:
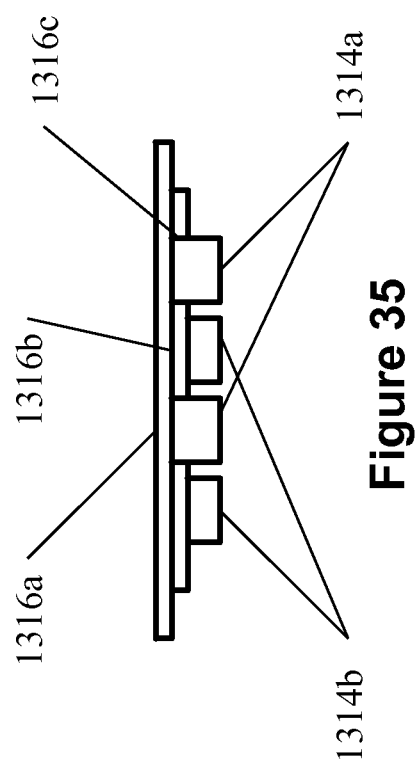
FIG. 35 illustrates a side view of a second variation of locking member for use with the dressing of FIG. 33.

Referring now to FIG. 35, as discussed above with regard to other embodiments of dressings, the dressing 1300 of FIG. 33 can be used such that the wound is closed in stages. FIG. 35 illustrates a restraining member 1314 for use with the dressing 1300 of FIG. 33 in which the restraining member 1314 is formed of first and second sets of restraining members 1314a, 1314b, each associated with a corresponding backing 1316a, 1316b. However, the restraining members 1314a are further disposed in corresponding openings 1316c in the backing 1316b, such that the backing 1316a and associated restraining members 1314a can be removed from the backing 1316b and associated restraining members 1314b. In this way, the backing 1316a and associated restraining members 1314a can be removed as discussed above to remove the bias in only a portion of the folds 1308a of the elastic member 1308 causing the elastic member 1308 to close the dressing about the wound a first predetermined amount. Subsequently, the backing 1316b and associated restraining members 1314b can be removed to remove the bias in the remaining folds 1308a of the elastic member 1308 causing the elastic members 1308 to close the dressing about the wound an additional predetermined amount. Of course, those skilled in the art will appreciate that more than two backings and associated restraining members can be utilized for several stages of closure. Furthermore, the portion of folds in which the bias is removed can be different or the same in each of the stages.

Figure 36:
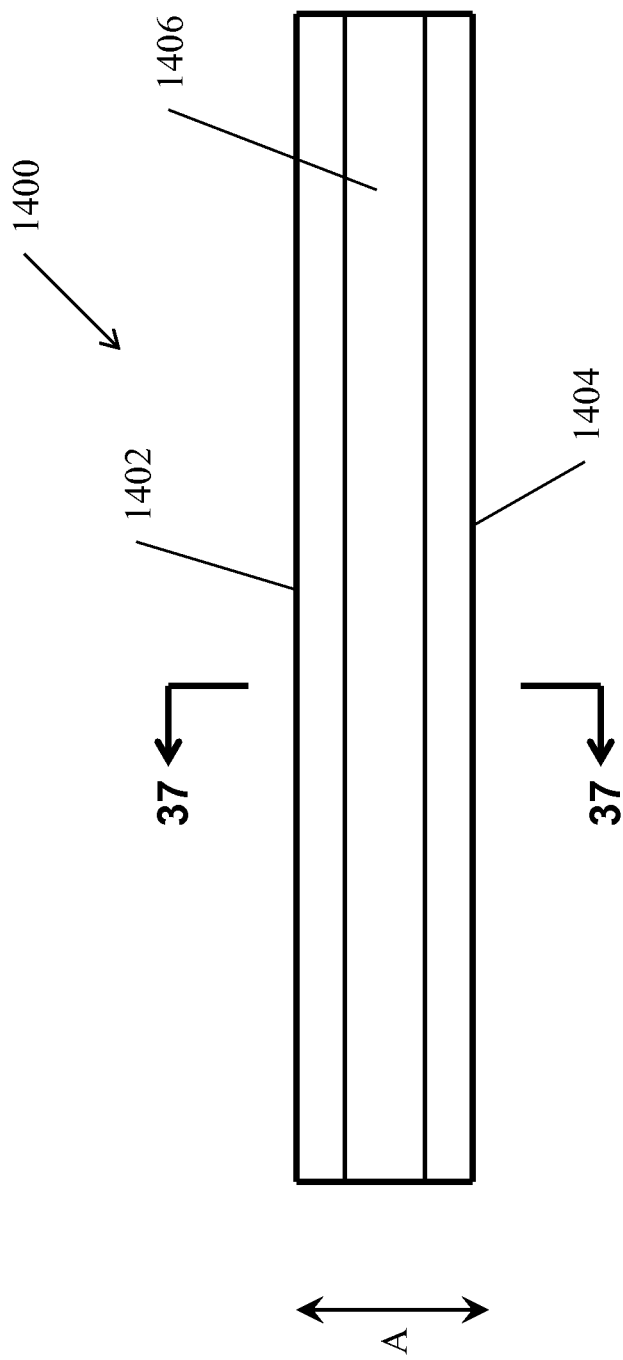
FIG. 36 illustrates a top view of an additional embodiment of a dressing for closing wounds.
Figure 37:
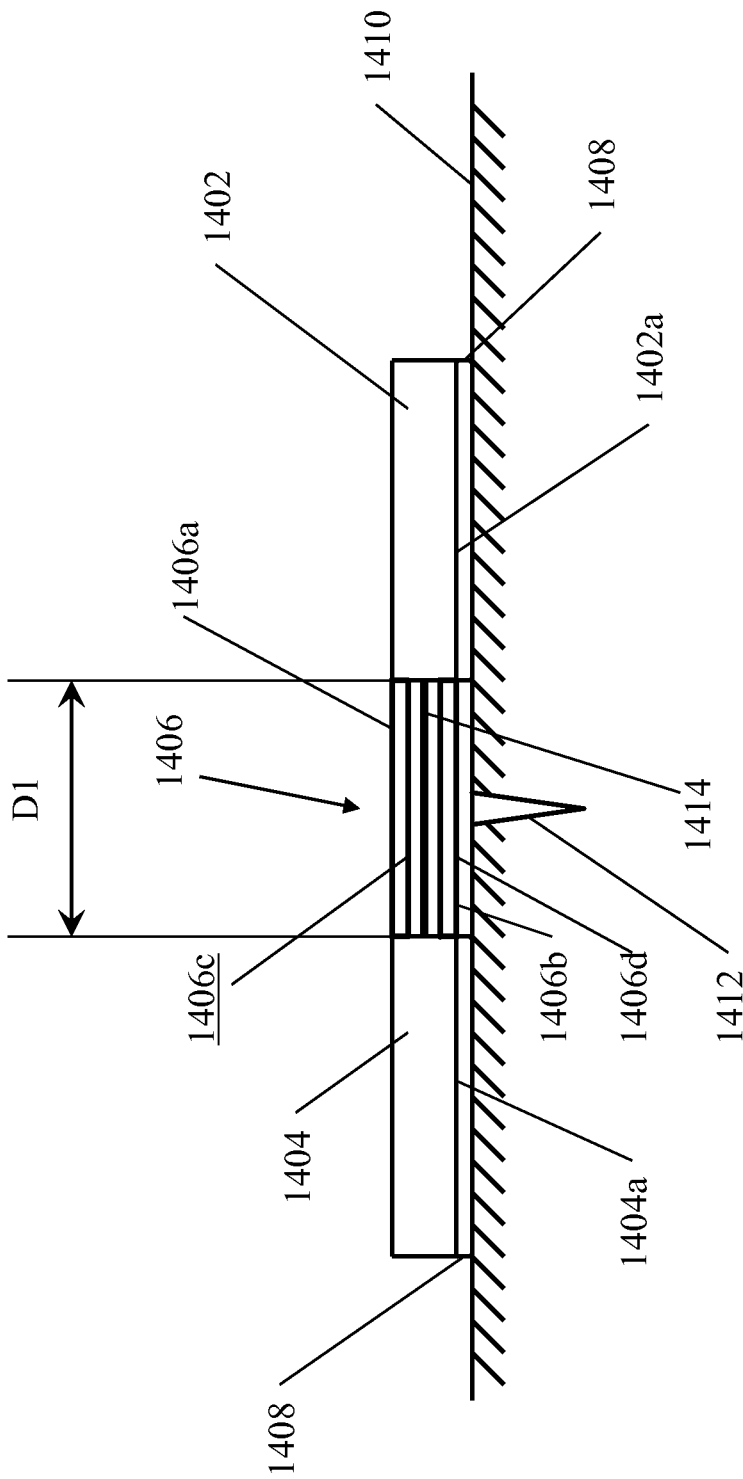
FIG. 37 illustrates a sectional view of the dressing of FIG. 36 as taken along line 37-37 where the locking member has not been removed and the wound is open.

Referring now to FIGS. 36 and 37, there is shown another embodiment of a dressing, generally referred to by reference numeral 1400. The dressing 1400 includes first and second bandage portions 1402, 1404 connected by an elastic material 1406 being elastic in at least a direction A towards the first and second bandage portions 1402, 1404 such that stretching the elastic material 1406 to pull the first and second bandage portions 1402, 1404 apart results in a biasing force tending to pull the first and second bandage portions 1402, 1404 together. The first and second bandage portions can be formed of a fabric or of a relatively rigid or semi-rigid material, such as a thin plastic sheet-like material. The elastic material 1406 can be formed of any material having elastic properties, such as an elastomer or a fabric having elastomer fibers woven in at least the direction A. An underside 1402a, 1404a of the first and second bandage portions 1402, 1404 corresponding to a surface of the skin to which the same are to be applied, include an adhesive 1408 for adhering the first and second bandage portions 1402, 1404 to the skin 1410. The elastic material 1406 includes upper and lower portions 1406a, 1406b to form a pocket 1406c. Although the pocket 1406c is illustrated as being formed by separate upper and lower portions, the pocket 1406c can also be formed in a loop, which can be enclosed and attached to the first and second portions by adhesive, sewing and the like. In use, the dressing 1400 is disposed on the skin 1410 such that a wound 1412 corresponds with the elastic material 1406. An underside 1406d of the elastic material may include a gauze material (not shown) for contact with the wound 1412.

A locking member 1414, such as the one shown in FIG. 39, is disposed in the pocket 1406c to maintain the elastic material 1406 in a stretched state (D1), as shown in FIG. 37. The locking member 1414 can be relatively rigid such that it maintains the elastic material 1406 in the stretched state (D1) without buckling (although some buckling may be permitted). The locking member may be formed with rounded corners 1414a such that it is less likely to catch on the elastic material 1406 during removal of the locking member 1414 from the pocket 1406c.

In use, a release layer (not shown in FIG. 37, but assumed to be similar to that shown in FIG. 9A, reference numeral 904) is releasably adhered to the adhesive on the underside of the first and second bandage portions 1402, 1404 such that it can be removed when the adhesive is to be adhered to the skin. As discussed above, the dressing 1400 is disposed on the skin 1410 such that a wound 1412 corresponds with the elastic material 1406. That is, the first and second bandage portions 1402, 1404 are adhered to the skin 1410 about the wound 1412 such the wound corresponds to the elastic material and the biasing direction of the elastic material 1406 would tend to close the wound 1412.

Figure 38:
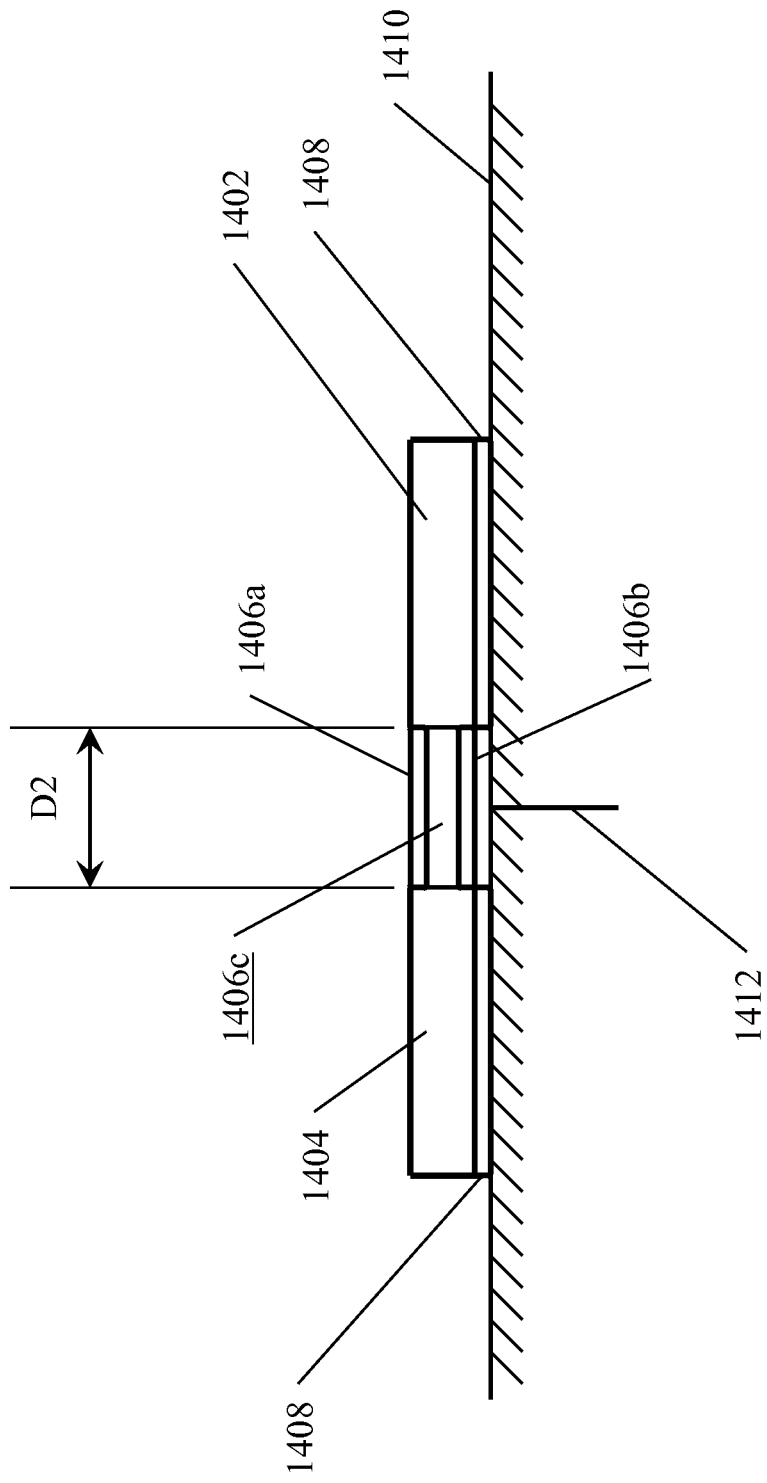
FIG. 38 illustrates the section view of FIG. 37 where the locking member has been removed and the wound is closed.

Referring now to FIG. 38, the locking member 1414 is removed by pulling it from the pocket 1406c causing the elastic material 1416 to pull the first and second bandage portions 1402, 1404 towards each other. The locking member 1414 may have a portion formed therein or attached thereto, such as a string or tab for facilitating the pulling of the same from the pocket 1406c. Since the first and second bandage portions 1402, 1404 are adhered to the skin 1410, the skin adhered to each of the first and second bandage portions 1402, 1404 is also pulled together, resulting in the wound 1412 closing (as shown in FIG. 38). The elastic material 1406 shrinks to a state D2 having a dimension across the wound 1412 smaller than the dimension in the state D1 shown in FIG. 37.

Figure 41:
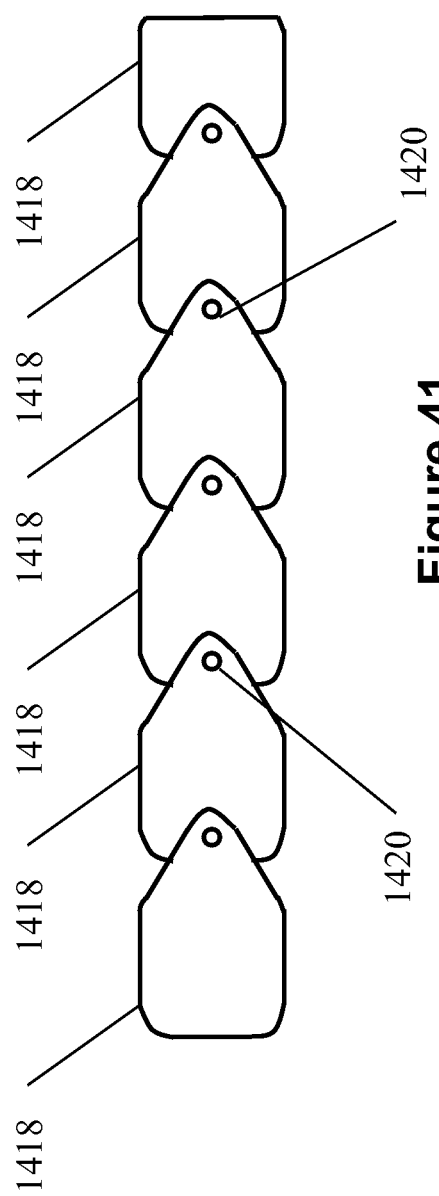
FIG. 41 illustrates another alternative locking member for use with the dressing of FIG. 36 to facilitate curving the same about an irregular shaped wound.

Similarly to the dressing illustrated in FIG. 31, the dressing 1400 can include notches (1218 in FIG. 31) formed on a periphery of the first and second bandage portions 1402, 1404 to facilitate curving the dressing about an irregularly shaped wound. In such a configuration, the locking member 1414 may be similarly notched or intermittently formed so as not to be a continuous member but formed of a series of locking members 1414b as shown in FIGS. 40a and 40b, which can be connected by a flexible member 1416, such as a string, fabric or the like. Forming the locking member non-continuous as a series of locking members 1414b also facilitates forming the dressing in a large roll and cutting the same to a desired length (between any two of the series of locking members 1414b). Alternatively, as shown in FIG. 41, the locking member may be intermittently formed with link portions 418 that are rotatable about pivots 420.

Similarly to that shown in FIG. 32 above, more than one locking member may be disposed in the pocket 1406c (or in a separate pocket corresponding to each of the locking members). Similarly to that shown in FIG. 32 above, the dressing can include a first locking member having a first width W1 and a second locking member having a second width W2. The second width W2 being smaller than the first width W1 such that after the first locking member is removed, the elastic material is restrained to only partially shrink. Subsequently, the second locking member can be removed to allow the elastic material to continue shrinking in the direction across the wound. Thus, the closure of the wound can be applied in stages (e.g., the removal of the first locking member can close the wound fully, however, after swelling subsides and the wound partially re-opens, the second locking member can be removed to fully close the wound once again). As discussed above, more than two locking members can be provided. Those skilled in the art will appreciate that the closure of the wound in stages can be accomplished without multiple locking members, for example, by allowing the locking member to be partially removed, such as by collapsing in the direction across the wound before being entirely removed or by having a varying width along its length.

Figure 42:
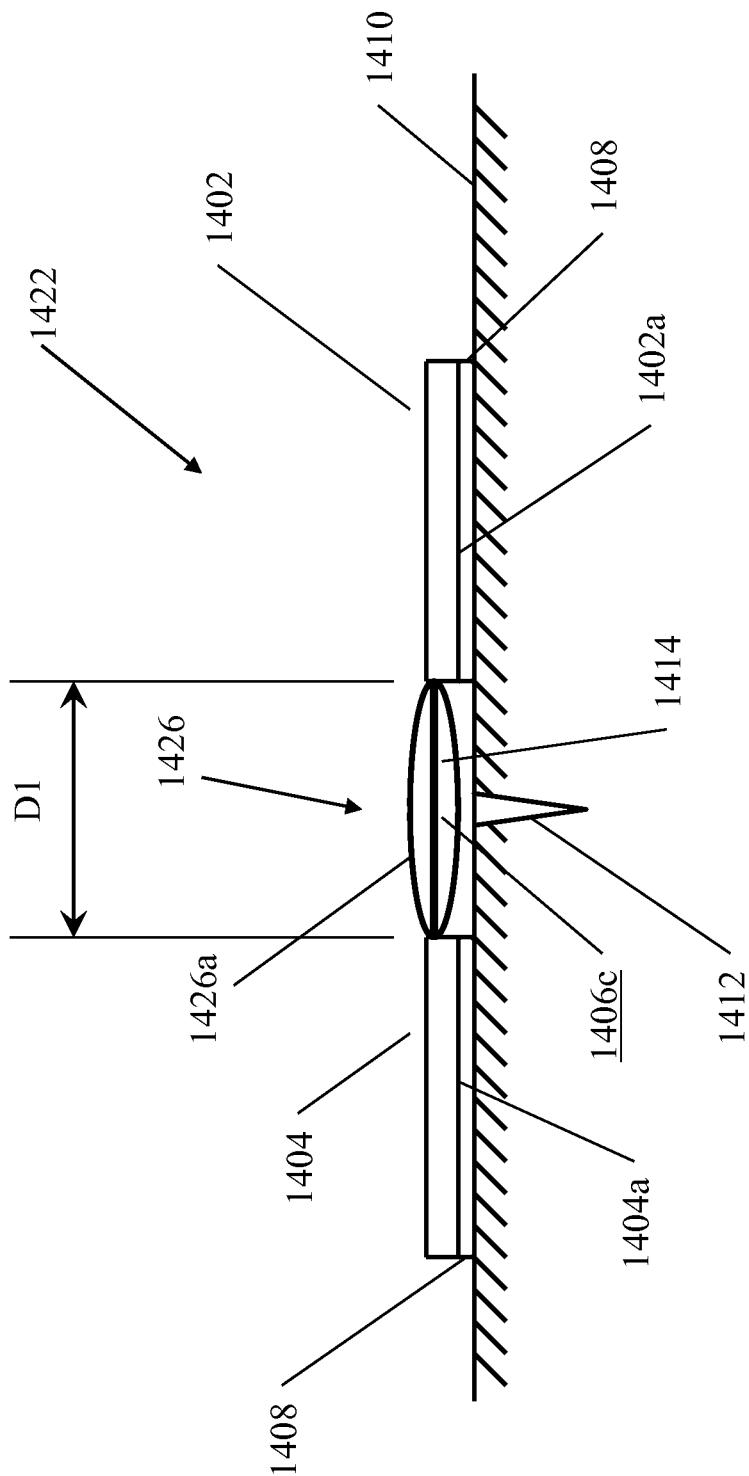
FIG. 42 illustrates a top view of a variation of the dressing for closing wounds shown in FIG. 36.

Referring now to FIG. 42, there is shown a variation of the dressing illustrated in FIGS. 36 and 37 in which like reference numerals refer to like features in FIGS. 36 and 37. The dressing of FIG. 42 being generally referred to by reference numeral 1422. Dressing 1422 includes the elastic material 1426 in the form of a loop 1426a, where the loop shape defines the cavity 1406c for insertion of the one or more locking members 1414. Any one of the locking members described above can be used with the dressing 1422 of FIG. 42. The loop 1426a shaped elastic material 1426 can be formed in a tube shape in a desired length corresponding to a width of the dressing (perpendicular to the stretching direction D1). Furthermore, the first and second bandage portions 1402, 1404 and elastic material 1426 of the dressing 1422 can be formed in separate pieces and fastened together by any means discussed above, such as stitching, adhering, fasteners etc. Alternatively, the first and second bandage portions 1402, 1404 and loop 1426a shaped elastic material 1426 can be formed in a single piece, such as by weaving the first and second bandage portions 1402, 1404 and elastic material 1426 together in one piece. In the latter construction, the elastic material may be the only portion woven with elastic fibers positioned in at least the stretching direction-D1 so as to be capable of stretching in direction D1.

Figure 43:
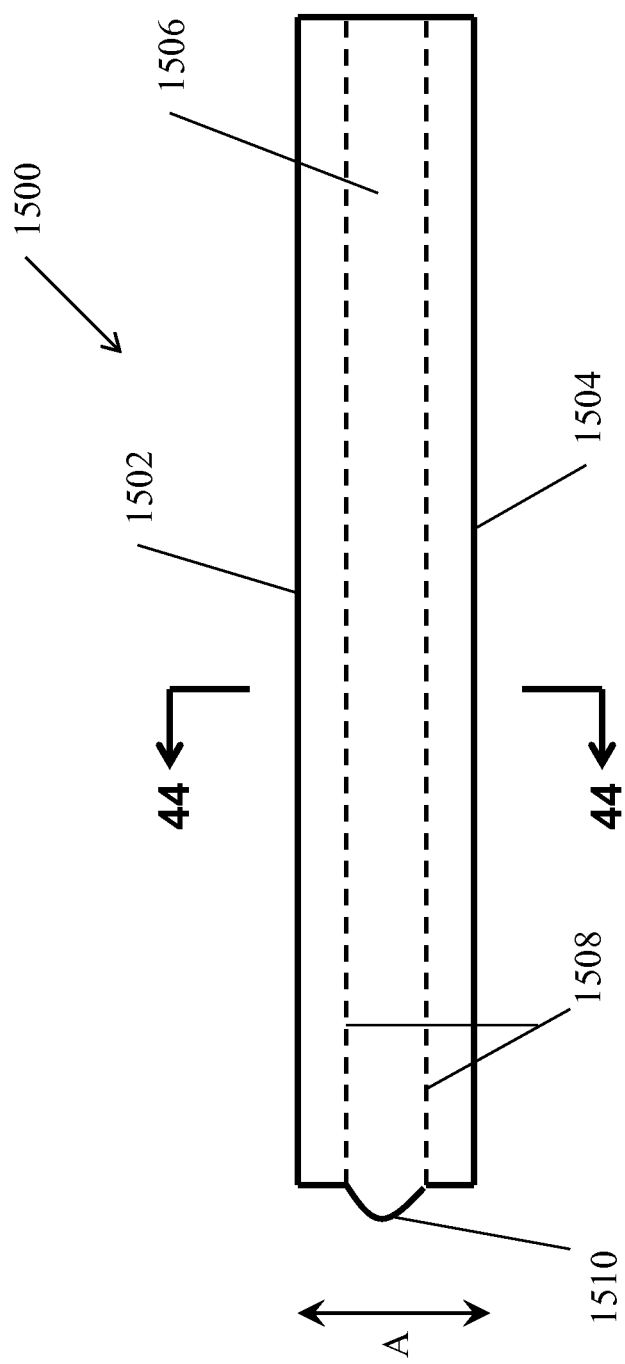
FIG. 43 illustrates a top view of an additional embodiment of a dressing for closing wounds.
Figure 44:
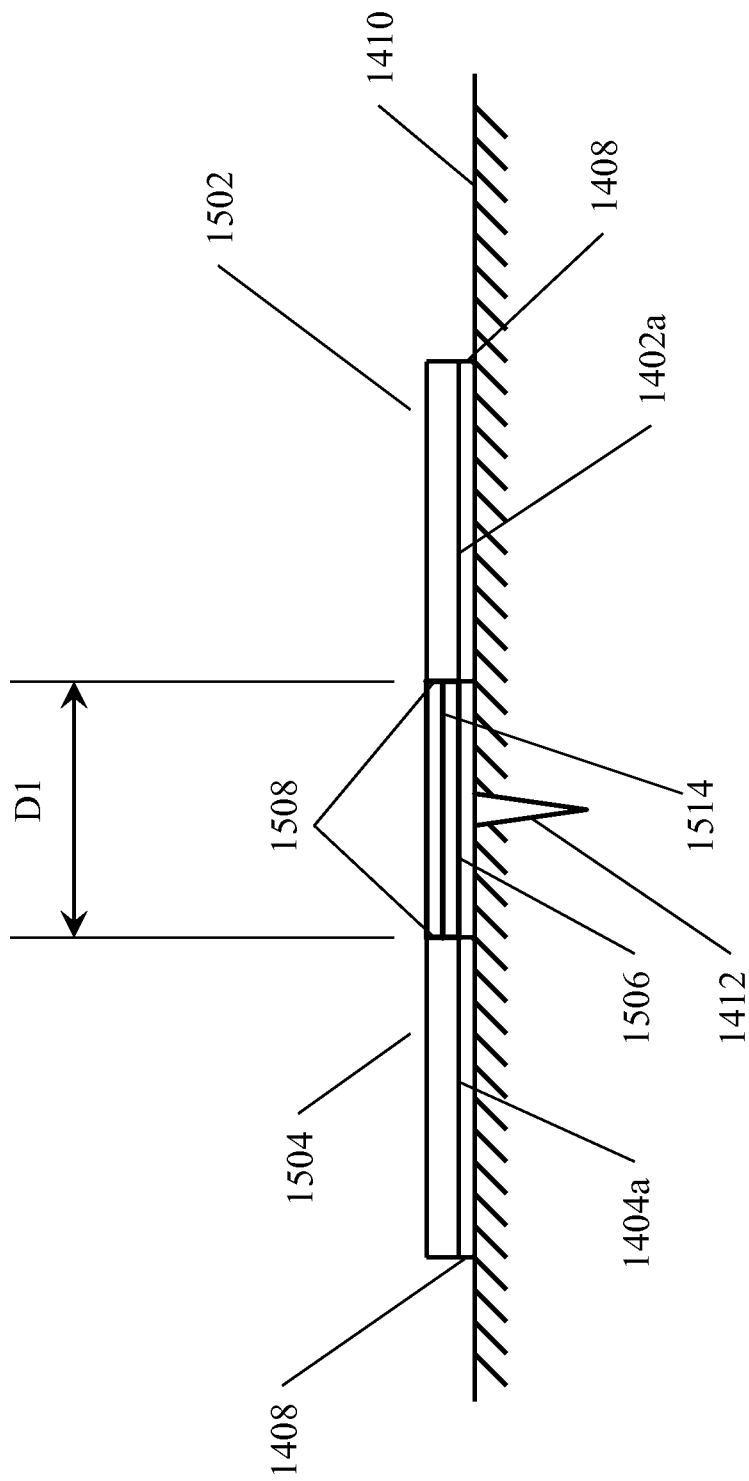
FIG. 44 illustrates a sectional view of the dressing of FIG. 43 as taken along line 44-44 where the locking member has not been removed and the wound is open.

Referring now to FIGS. 43 and 44, there is shown another embodiment of a dressing, generally referred to by reference numeral 1500, in which like reference numerals illustrate like features to those illustrated in FIGS. 36 and 37. In dressing 1500, the locking member 1514 is integrally formed with at least a surface of the first and second bandage portions 1502, 1504 and includes a perforation (or other weakened portion) 1508 such that the elastic material 1506 is retained in a stretched state (dimension D1). After adhering the dressing 1500 to the skin 1410 about the wound 1412, the locking member 1508 can be torn along the perforations 1508 or otherwise removed from the first and second bandage members 1502, 1504. After such locking member 1514 is removed, the elastic material 1506 is allowed to pull the wound 1412 together as it pulls the first and second bandage portions 1502, 1504 towards each other due to the biasing of the elastic material 1506 (similarly to that shown in FIG. 37). A tab 1510 or other projection can be provided to facilitate removal of the locking member 1508 from the first and second bandage portions 1502, 1504.

Any of the dressings described above may be provided with a medicament, such as for promoting healing, reducing inflammation, fighting infection etc.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A dressing for application to skin, the dressing comprising:
   first and second portions;
   an adhesive applied on a surface of the first and second portions for adhering the first and second portions to the skin;
   an elastic member having one end connected to the first portion and another end connected to the second portion, the elastic member having portions defining a pocket; and
   a locking member having a cross-sectional shape entirely disposed in the pocket for restraining the elastic member into a first shape;
   wherein when the locking member is at least partially removed from the pocket, the elastic member moves in a direction towards an unrestrained second shape;
   the locking member is formed of a series of locking members connected by a flexible member; and
   the flexible member is one of a string or fabric.

2. The dressing of claim 1, wherein the locking member is rectangular in shape and has rounded corners.

3. The dressing of claim 1, wherein the elastic member is formed in a loop shape.

4. The dressing of claim 3, wherein the elastic member and first and second rectangular portions are formed separately and connected together with the elastic portion being disposed between the first and second rectangular portions.

5. The dressing of claim 3, wherein the elastic member and first and second rectangular portions are integrally formed in a single piece.

6. The dressing of claim 5, wherein the elastic member and first and second rectangular portions are woven in the single piece.

7. The dressing of claim 6, wherein only the elastic portion of the single piece is woven with elastic fibers in a direction from the end of the first rectangular portion to the end of the second rectangular portion.

* * * * *